(12) United States Patent
Shmilovich et al.

(10) Patent No.: US 12,711,420 B2
(45) Date of Patent: Aug. 18, 2026

(54) ORBITAL MIXER MACHINE LEARNING METHOD FOR PREDICTING AN ELECTRONIC STRUCTURE OF AN ATOMIC SYSTEM

(71) Applicant: Robert Bosch GmbH, Stuttgart (DE)

(72) Inventors: Kirill Shmilovich, Milwaukee, WI (US); Ivan Batalov, Pittsburgh, PA (US); Jeremy Kolter, Pittsburgh, PA (US); Mordechai Kornbluth, Brighton, MA (US); Jonathan Mailoa, Cambridge, MA (US); Devin Willmott, Pittsburgh, PA (US)

(73) Assignee: Robert Bosch GmbH, Stuttgart (DE)

( * ) Notice: Subject to any disclaimer, the term of this patent is extended or adjusted under 35 U.S.C. 154(b) by 1141 days.

(21) Appl. No.: 17/737,733

(22) Filed: May 5, 2022

(65) Prior Publication Data

US 2023/0359929 A1 Nov. 9, 2023

(51) Int. Cl.

*G06N 20/00* (2019.01)
*G16C 20/30* (2019.01)
*G16C 20/70* (2019.01)

(52) U.S. Cl.

CPC ............ *G06N 20/00* (2019.01); *G16C 20/30* (2019.02); *G16C 20/70* (2019.02)

(58) Field of Classification Search

CPC .......... G06N 20/00; G06N 3/084; G06N 3/09; G06N 3/045; G16C 20/30; G16C 20/70

See application file for complete search history.

(56) References Cited

U.S. PATENT DOCUMENTS

2020/0167439 A1* 5/2020 Mailoa .................... G06F 30/20
2020/0176087 A1* 6/2020 Colby .................... G06N 3/045

(Continued)

FOREIGN PATENT DOCUMENTS

WO WO-2021243106 A1 * 12/2021 ............ G06N 3/044

OTHER PUBLICATIONS

[Submitted on May 2, 2017 (v1), last revised May 3, 2017 (this version, v2)] Machine learning reveals orbital interaction in crystalline materials Tien Lam Pham, Hiori Kino, Kiyoyuki Terakura, Takashi Miyake, Ichigaku Takigawa, Koji Tsuda, Hieu Chi Dam, Cite as: arXiv:1705.01043 [cond-mat.mtrl-sci] (Year: 2017).*

(Continued)

*Primary Examiner* — Sun M Li
(74) *Attorney, Agent, or Firm* — Brooks Kushman P.C.

(57) ABSTRACT

A machine learning (ML) method for predicting an electronic structure of an atomic system. The method includes receiving an atomic identifier and an atomic position for atoms in the atomic system; receiving a basis set including rules for forming atomic orbitals of the atomic system; forming the atomic orbitals of the atomic system; and predicting an electronic structure of the atomic system based on the atom identifier, the atom position for the atoms in the atomic system, and the atomic orbitals of the atomic system. The ML method is capable of extremely accurate and fast molecular property prediction. The ML can directly purpose basis dependent information to predict molecular electronic structure. The ML method, which may be referred to as an orbital mixer model, uses multi-layer perception (MLP) mixer layers within a simple, intuitive, and scalable architecture to achieve competitive Hamiltonian and molecular orbital energy and coefficient prediction accuracies.

20 Claims, 27 Drawing Sheets

(56) References Cited

U.S. PATENT DOCUMENTS

| | | | | |
|---|---|---|---|---|
| 2020/0294630 | A1* | 9/2020 | Miller | G16C 20/10 |
| 2021/0081834 | A1* | 3/2021 | Hegde | G06N 3/0475 |
| 2023/0088979 | A1* | 3/2023 | Neogi | G01R 31/2648 702/189 |
| 2023/0095631 | A1* | 3/2023 | Ganeshan | G06N 3/04 702/22 |
| 2024/0071577 | A1* | 2/2024 | Kirkpatrick | G16C 20/30 |
| 2024/0387004 | A1* | 11/2024 | Hanaoka | G16C 20/50 |
| 2025/0022548 | A1* | 1/2025 | Fukuta | G06N 20/00 |

OTHER PUBLICATIONS

Schütt KT, Gastegger M, Tkatchenko A, Müller KR, Maurer RJ. Unifying machine learning and quantum chemistry with a deep neural network for molecular wavefunctions. Nat Commun. Nov. 15, 2019;10(1):5024. doi: 10.1038/s41467-019-12875-2. PMID: 31729373; PMCID: PMC6858523. (Year: 2019).*

Balachandran PV, Theiler J, Rondinelli JM, Lookman T. Materials Prediction via Classification Learning. Sci Rep. Aug. 25, 2015;5:13285. doi: 10.1038/srep13285. PMID: 26304800; PMCID: PMC4548442. (Year: 2015).*

Lam Pham T, Kino H, Terakura K, Miyake T, Tsuda K, Takigawa I, Chi Dam H. Machine learning reveals orbital interaction in materials. Sci Technol Adv Mater. Oct. 26, 2017;18(1):756-765. doi: 10.1080/14686996.2017.1378060. PMID: 29152012; PMCID: PMC5678453. (Year: 2017).*

Schütt, K. T et al., “Unifying machine learning and quantum chemistry with a deep neural network for molecular wavefunctions,” Nature Communications, vol. 10, No. 5024, Nov. 15, 2019, DOI: 10.1038/s41467-019-12875-2.

Tolstikhin, I. et al., “MLP-Mixer: An all-MLP Architecture for Vision,” 35th Conference on Neural Information Processing Systems (NeurIPS 2021), 2021, https://arxiv.org/abs/2105.01601.

Unke, O. T., et al., “SE(3)-equivariant prediction of molecular wavefunctions and electronic densities,” 35th Conference on Neural Information Processing Systems (NeurIPS 2021), 2021, https://arxiv.org/abs/2105.01601.

* cited by examiner

ORBITAL MIXER MACHINE LEARNING METHOD FOR PREDICTING AN ELECTRONIC STRUCTURE OF AN ATOMIC SYSTEM

TECHNICAL FIELD

The present disclosure relates to a machine learning method for predicts an electronic structure of an atomic system. The machine learning method may be a deep neural network. The machine learning method may use atomic orbitals as input.

BACKGROUND

An explosion of interest has surrounded applying machine learning methods to quantum chemistry with a plethora of interesting application areas such as learning interatomic potentials, predicting spectroscopic properties, optoelectric properties, activation energies, and a variety of physical properties throughout the chemical compound space. Quantum chemistry workflows can obtain such chemical and physical information by modelling the electronic Schrodinger equation in a chosen basis set of localized atomic orbitals that is then used to derive the ground-state molecular wavefunction. Machine learning can be used to directly predict the molecular electronic structure which then provides access to a plethora of these derived properties without needing to train specialized models for each property of interest. Previous proposals such as the SchNOrb model and most recently the PhiSNet model present deep learning architectures for predicting molecular wavefunctions and electronic densities by purposing only information of the atomic coordinates and molecular composition. Though inputs to these models rely only on the raw features of the molecule, they are trained on molecular wavefunctions from real quantum chemistry calculations, which necessarily associates the model's predictions with a prescribed basis.

SUMMARY

According to one embodiment, a machine learning method for predicting an electronic structure of an atomic system is disclosed. The method includes receiving an atomic identifier and an atomic position for atoms in the atomic system. The method further includes receiving a basis set including rules for forming atomic orbitals of the atomic system. The method also includes forming the atomic orbitals of the atomic system. The method further includes predicting an electronic structure of the atomic system based on the atom identifier, the atom position for the atoms in the atomic system, and the atomic orbitals of the atomic system.

According to another embodiment, a machine learning training method for training parameters of a machine learning model for predicting an electronic structure of an atomic system. The method includes receiving a true electronic structure of the atomic system; receiving a basis set including rules for forming first and second atomic orbitals of the atomic system; predicting a predicted electronic structure of the atomic system by performing a forward pass through the machine learning model using the basis set; determining a loss by comparing the true electronic structure and the predicted electronic structure of the atomic system; and training the machine learning model by updating the parameters of the machine learning model based on the loss and a machine learning optimizer.

According to yet another embodiment, a machine learning method for predicting molecular orbital characteristics of a molecule is disclosed. The method includes receiving atomic positions and atomic identifiers of atoms in the molecule; receiving a basis set including rules for forming atomic orbitals of the molecule; predicting a predicted electronic structure and calculating an overlap matrix of the molecule by performing a forward pass using the atomic positions, the atomic identifiers, and the basis set; and predicting the molecular orbital characteristics based on the predicted electronic structure and the overlap matrix.

DETAILED DESCRIPTION

Figure 1A:
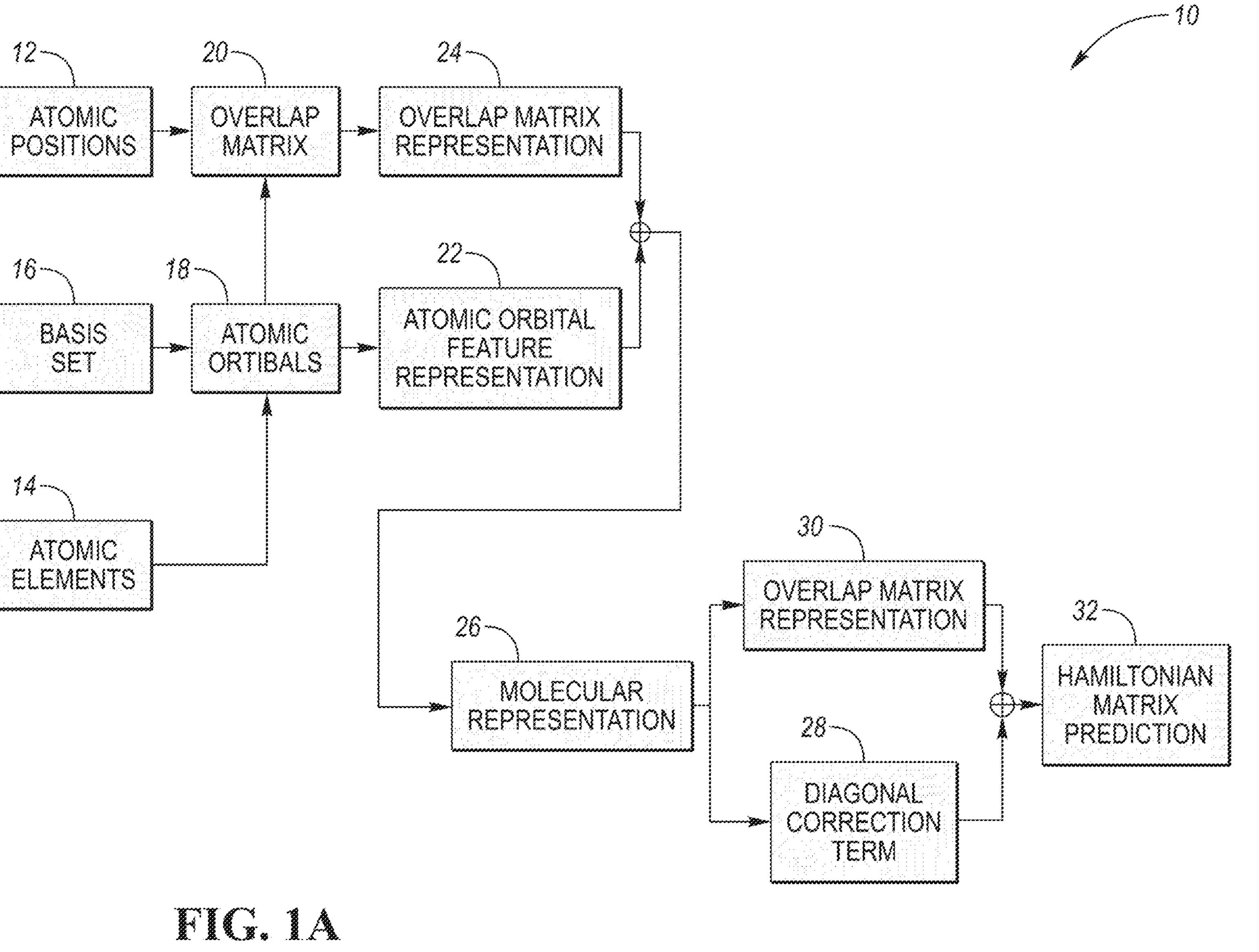
FIG. 1A depicts a flowchart of a forward pass machine learning algorithm configured to pass input forward through a machine learning model to obtain an output.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the term "polymer" includes "oligomer," "copolymer," "terpolymer," and the like; the description of a group or class of materials as suitable or preferred for a given purpose in connection with the invention implies that mixtures of any two or more of the members of the group or class are equally suitable or preferred; molecular weights provided for any polymers refers to number average molecular weight; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

This invention is not limited to the specific embodiments and methods described below, as specific components and/or conditions may, of course, vary. Furthermore, the terminology used herein is used only for the purpose of describing embodiments of the present invention and is not intended to be limiting in any way.

As used in the specification and the appended claims, the singular form "a," "an," and "the" comprise plural referents unless the context clearly indicates otherwise. For example, reference to a component in the singular is intended to comprise a plurality of components.

Except where expressly indicated, all numerical quantities in this description indicating dimensions or material properties are to be understood as modified by the word "about" in describing the broadest scope of the present disclosure.

The first definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

The term "substantially" may be used herein to describe disclosed or claimed embodiments. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

Reference is being made in detail to compositions, embodiments, and methods of embodiments known to the inventors. However, disclosed embodiments are merely exemplary of the present disclosure which may be embodied in various and alternative forms. Therefore, specific details disclosed herein are not to be interpreted as limiting, rather merely as representative bases for teaching one skilled in the art to variously employ the present disclosure.

Machine learning for molecular inference has experienced impressive success in recent years, showcasing spectacular predictive accuracy enabled by large quantities of ab initio data, the incorporation of prior physical and chemical knowledge, and invariant and/or equivariant architectures. A common paradigm of these works interprets molecules as connected graphs and uses message passing to model interactions as a function of single-particle contributions. A variety of increasingly complex graph convolutional operations have been proposed for these purposes, such as the work of the SchNet model introducing continuous filter convolutions, the message passing designed based on physical principles and attention of the PhysNet model, the explicitly covariant network operations of the Cormorant model, the Tensor field networks. While these models have demonstrated expressively and accuracy for molecular property prediction, each network is trained to predict only a predetermined set of scalar, vector, or sometimes tensor quantities. This fundamental design of these networks therefore requires training separate bespoke models for each molecular property of interest.

In contrast, a recent line of proposals strives instead to ascertain molecular wavefunctions by predicting the Hamiltonian matrix that satisfies the electronic Schrodinger equation from which physical and chemical properties can be derived. The short history of these methods begins with the Hedge and Bowen model, where they predict a Hamiltonian for two simple copper and carbon (e.g., diamond) systems using kernel ridge regression. Then a deep learning architecture called SchNet for Orbital (SchNOrb) was proposed that uses the SchNet architecture and pair-wise features to predict the Hamiltonian block-wise, establishing baselines for molecule configurations from the MD17 dataset. Follow-up work improved accuracy on select molecules by applying the SchNOrb model trained on a minimal basis set representation of molecular wavefunctions. More recently, the PhiSNet model has been proposed. The PhiSNet model draws upon insights of SE(3)-equivariant models to maintain that Hamiltonian predictions remain explicitly covariant with respect to rigid rotations or translations while also reporting significantly improved prediction accuracies. Notably, another proposal devises similarly equivariant Hamiltonian representations for uses in other applications such as kernel machines.

Architectural choices around modeling interactions between atoms and other molecular are of central interest in the design of neural networks for molecular inference. The afore-mentioned common choices of graph neural network structure or convolution/mixing operation dependent on pair-wise atomic distances have the benefit of incorporating geometric information into the structure of the network and prioritizing local interactions. These approaches come at the cost of additional hyperparameters or increased network complexity, and frequently requires imposing a distance cutoff that prevents the network from directly modeling long-range atomic interactions.

In one or more embodiments, the orbital mixer model draws on approaches for mixing spatial information from other deep learning domains, namely those from computer vision, where vision transformers (ViTs) have prompted rethinking of the standard approach of convolutional networks (CNNs). The orbital mixer model of one or more embodiments is directly based on the MLP mixer vision architecture, a competitive but dramatically simpler alternative to both ViTs and CNNs. The MLP mixer architecture splits an input image into patches and alternates between patch-wise and channel-wise mixing operations via simple multi-layer perception (MLP) layers. By replacing image patches with atomic orbital and overlap matrix information, the orbital mixer model of one or more embodiments is obtained and is configured to learn atomic interactions at any range without the need for complex or hand-engineered mixing operations. The favorable complexity of MLP layers as compared to graph transformers is a benefit in the molecular inference domain, where scalability to larger systems is particularly desirable.

Electronic structure calculations typically represent electrons in a basis-set of atomic orbitals $$(AO)\{|\phi_i\rangle\}_{i=1}^{i=N_{orbs}}$$

meant to describe the available electron orbitals of the system. The bracket notation x is used to represent a quantum state in the complex Hilbert space. In the Hartree-Fock (HF) model, the electron energies are given by the Hartree-Fock equations, represented in matrix form as FC=SCE, which determine the molecular orbital (MO) wavefunctions $$|\varphi_m \sum_{i=1}^{i=Norbs} C_{im}|\phi_i$$

and ther associated MO energies $\in_m=E_{mm}$, where E is a diagonal matrix. Electrons populate the lowest energy MOs in accordance with the Pauli exclusion principle, which then define the electronic and chemical properties of the system. The Hamiltonian F in FC=SCE approximates the single-electron energy operator $\hat{F}$ within the set of basis functions $\{\phi_i|\phi_j\}$ with matrix elements defined as $F_{ij}=\langle\phi_i|\hat{F}|\phi_j\rangle$, while the overlap matrix S describes the relationships between the different basis functions via the inner product $S_{ij}=\langle\phi_i|\phi_j\rangle$. The formulation for density-functional theory (DFT) is almost identical, with the replacement of the Kohn-Sham Hamiltonian for the Fock matrix and Kohn-Sham orbitals for molecular wavefunctions. The F matrix or the term "Hamiltonian" are used for either according to one or more embodiments.

The generalized eigenvalue problem in FC=SCE can be solved to determine the electron density $D_{ij}=\Sigma_k C_{ik} C_{jk}$, where the summation is carried over the k indexing the lowest energy MOs which are occupied. The remaining unoccupied orbitals that do not enter the density matrix calculations are called virtual orbitals and are only defined up to an arbitrary unitary transformation. However, the matrix elements $F_{ij}$ themselves depend on the electron density D requiring that FC=SCE be solved in a self-consistent manner. Typically, DFT and HF begin with an initial guess for the electron density D and/or orbital occupations C, followed by an iterative procedure that alternatingly (1) uses the density estimate D to calculate the Hamiltonian F and (2) solves FC=SCE to yield an improved estimate for the electron density, until some convergence criteria is met. The major source of computational expense in DFT comes from the number of these self-consistent iterations that must be performed to obtain converged electron density estimates that may in turn be used in downstream quantum chemical calculations.

While in principle the eigenvectors C and eigenvalues E contain the same information as the Hamiltonian F and the overlap matrix S, using machine language to directly predict C and E is complicated by possible state degeneracies and the coefficients being defined only up to an arbitrary phase. In contrast, the Hamiltonian F is better behaved as a smooth function of the atomic coordinates, and combined with S and FC=SCE, can be used to determine C and E. These properties make the Hamiltonian F a more suitable target for machine learning enabled prediction. The goal is therefore to learn to reliably predict the Hamiltonian F for a given molecular configuration and thereby alleviating some computational expense required in self-consistently solving Eqn. FC=SCE.

Methods are known for predicting an electronic structure of a molecule or other atomic system using a neural network. For example, a method of unifying machine learning and quantum chemistry with a deep neural network for molecular wavefunctions has been proposed. Another proposal encompasses equivariant prediction of molecular wavefunctions and electronic densities. These proposals require labeled training sets. The labeled training sets are derived by performing density functional theory (DFT) calculations on many molecules to obtain molecular energies and coefficients. Given the labeled training set, these methods train a neural network, where the input is basic information about the molecule (e.g., atomic number and position of each atom) and the output is a prediction of the electronic structure of the molecule (e.g., in the form of either Fock matrix entries or molecular orbitals energies and coefficients).

In one or more embodiments, a machine learning model is presented to predict molecular orbitals that explicitly supplies basis set-specific information as input to a deep learning architecture that models interactions of atomic orbitals representations. Compared to only atomic coordinates and molecular composition, a complete basis set can provide a much higher dimensional and information rich representation of a molecular configuration. The machine learning model of one or more embodiments, sometimes referred to herein as the orbital mixer model, purposes characteristics of the atomic orbitals jointly with their spatial overlap to predict the orbital coefficients that define the molecular electron density. The orbital mixer architecture uses MLP mixer layers to efficiently model interactions between atomic orbital representations, and to ultimately predict the electronic Hamiltonian F for a molecular configuration, which can be diagonalized to obtain molecular orbitals. Directly operating on atomic orbital representations provides a strong inductive bias for the orbital mixer model when predicting the Hamiltonian F, which is represented in the same atomic orbital basis.

One or more embodiments disclose a machine learning method for predicting an electronic structure of an atomic system (e.g., a molecule) using atomic orbitals. DFT calculations make use of the concept of atomic orbitals, which are functions that describe the locations of electrons in an atom. DFT calculations include a determination of how atomic orbitals interact with each other to affect the total energy of the atomic system. In one or more embodiments, a basis set is input and includes a number (e.g., set of two or more) of rules for selecting a number of atomic orbitals used in the DFT calculations. The number of atomic orbitals using a basis set makes the use of a machine learning method (e.g., a deep neural network) less computational demanding than the conventional methods disclosed above.

When the conventional methods disclosed above train neural networks, the methods only use information about the molecule itself (e.g., the type of atom and position of each atom) as the input. However, since the creation of the training data affects the output of the machine learning model, the machine learning model indirectly and implicitly learns how these atomic orbitals are combined to form the output of the machine learning model.

In contrast, the machine learning methods of one or more embodiments use both molecular information (e.g., atomic elements and atomic positions) and basis set atomic orbital input. The basis set atomic orbital input provides richer information about the overall configuration of the molecule than the molecular information only.

The machine learning methods of one or more embodiments have one or more benefits. By explicitly including information about a basis set and atomic orbitals while training the machine learning model, the trained model has a stronger inductive bias, thereby allowing quicker training (e.g., less computationally demanding) and/or more accurate prediction of an electronic structure of a molecule. The computational time to generate the additional information of the basis set and the atomic orbitals is negligible compared to the time to train a typical trainable model. The machine learning methods of one or more embodiments may have better complexity as the number of atoms in the atomic system increases compared to the conventional methods disclosed above because the machine learning methods of one or more embodiments is relatively simpler in application. The machine learning methods of one or more embodiments may run atomic simulations (e.g., a simulation of a molecule or other atomic system over time to determine, for example, when and how chemical reactions will occur). Once the machine learning model is trained, the trained machine learning model may be used as a solver in an atomic simulator. Such atomic simulator runs much faster (e.g., several orders of magnitude faster) than a quantum mechanics tool such as DFT.

FIG. 1A depicts a flowchart of forward pass machine learning algorithm 10 configured to pass input forward through a machine learning model to obtain an output. FIG. 1A depicts operations 12, 14, and 16 relating to inputs of forward pass machine learning algorithm 10. Operation 12 represents an input of the atomic positions of a number of atoms in a molecule. Operation 14 represents an input of the atomic identifier (e.g., the element) of a number of atoms in the molecule. Operation 16 includes the input of a basis set including a number (e.g., a set of two or more) of rules. As depicted in operation 18, the basis set is used to form a number (e.g., a set of two or more) of atomic orbitals given the atom of the molecule.

As depicted in operation 20, the number of atomics orbitals and the atomic positions are used to form an overlap matrix. The overlap matrix may be a matrix where entries $(i_n,j_n)$ are between 0 and 1, where entry (i,j) represents how much atomic orbitals i and j overlap in space (1 if the i and j atomic orbitals are identical, 0 if the atomic orbitals do not overlap at all).

As depicted in operation 22, a multi-feature embedding is determined for each atomic orbital by embedding a number of categorical features of the atomic orbital (e.g., atom type and quantum numbers) to form a number of embedded features and summing the number of embedded categorical features. The multi-feature embedding is configured to enhance the performance of the machine learning model.

As depicted in operation 24, a linear transformation is applied to each row of the overlap matrix to obtain an overlap matrix representation. The overlap matrix representation is passed through $L_1$ multi-layer perception (MLP) mixer layers. The MLP mixer layers may be a parameter-efficient method for mixing representations in a neural network. The MLP mixer architecture splits an input image into patches and alternates between patch-wise and channel-wise mixing operations via simple multi-layer perception (MLP) layers.

As depicted in operation 26, the multi-feature atomic orbital embeddings output from operation 22 and the overlap matrix representation of operation 24 are summed to obtain a molecular representation.

As depicted in operation 28, a linear transformation is applied to each row of the molecular representation to obtain a diagonal correction term. Operation 28 may further include passing the molecular representation through $L_2$ additional MLP mixer layers to obtain a mixer layer output. A linear transformation may be applied to the mixer layer output to obtain a refined molecular representation. Operation 28 may further include adding the diagonal correction term to the diagonal of the refined molecular representation to obtain a diagonal-corrected refined molecular representation.

As depicted in operation 30, the transpose of the diagonal-corrected refined molecular representation is added to itself to determine if the matrix is symmetric, thereby providing a predicted Hamiltonian matrix.

Figure 1B:
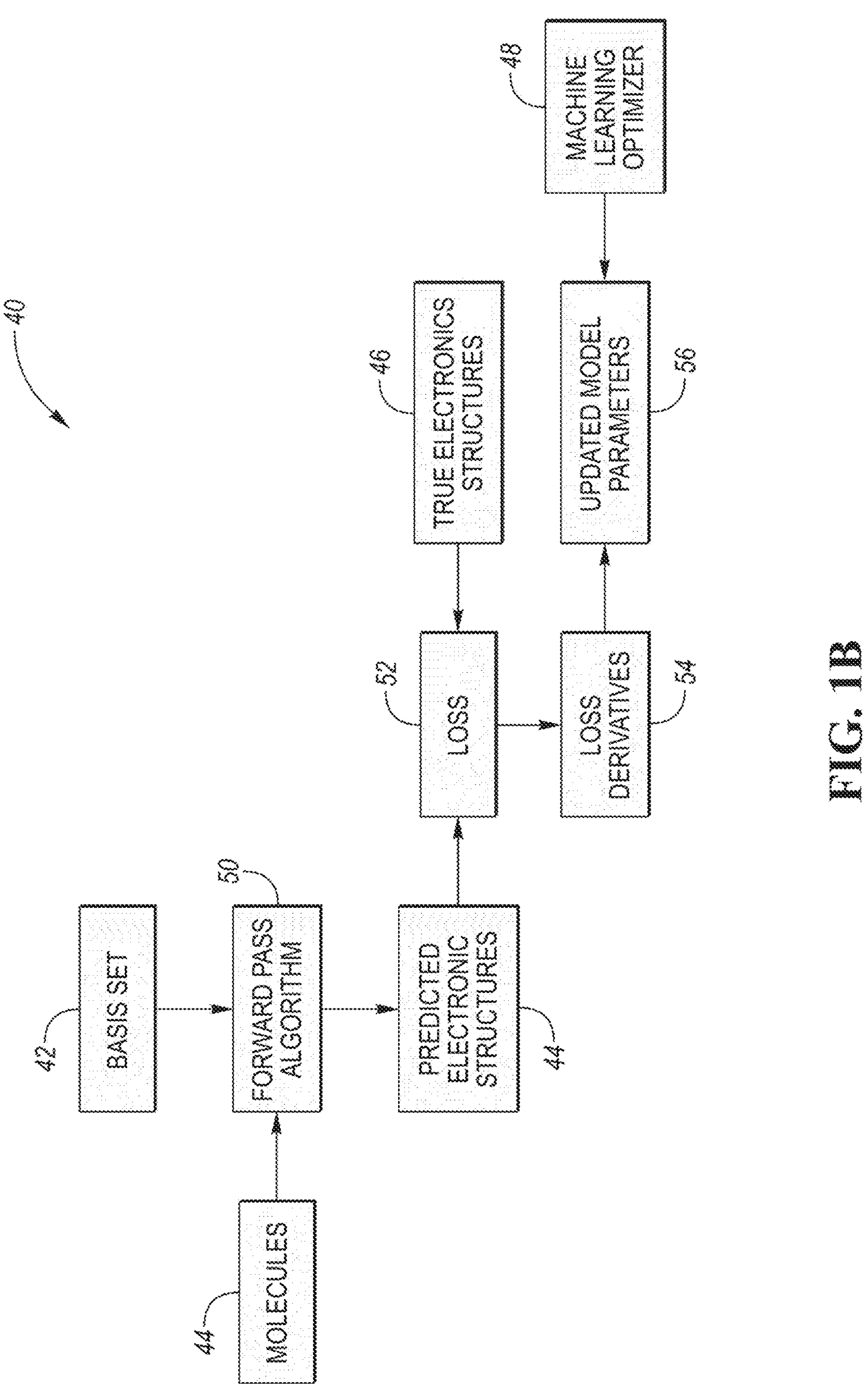
FIG. 1B depicts a flowchart of a machine learning training model configured to use the output of a forward pass machine learning algorithm to train parameters of a machine learning model (e.g., a deep neural network).

FIG. 1B depicts a flowchart of machine learning training model 40 configured to use the output of forward pass machine learning algorithm 10 to train a number of parameters of a machine learning model (e.g., a deep neural network).

FIG. 1B depicts operations 42, 44, 46, and 48 relating to inputs of machine learning training model 40. Operation 42 represents an input of basis set including a number (e.g., a set of two or more) of rules for forming a number (e.g., a set of two or more) of atomic orbitals given the atoms of a molecule. Operation 44 represents an input of a number of molecules. Operation 46 represents an input of a true electronic structure of the number of molecules. The true electronic structures may be a true Hamiltonian matrix associated with each input molecule. Operation 48 represents an input of a machine learning optimizer (e.g., a deep learning optimizer, ADAM adaptive learning rate optimizer algorithm, or stochastic gradient descent).

As depicted in operation 50, a forward pass through the trainable machine learning model is performed on the number of molecules. The result of this operation is a predicted electronic structure (e.g., a predicted Hamiltonian matrix) for the number of molecules, as represented by operation 52. This operation may be performed for two or more molecules in the number of molecules in a parallel operation.

As depicted in operation 52, a loss is obtained by comparing the predicted electronic structure (e.g., a predicted Hamiltonian matrix) and the true electronic structure (e.g., a true Hamiltonian matrix) for the molecule. The loss may be a mean squared error of the difference between the predicted and true electronic structures.

As depicted in operation 54, the operation of backpropagating through the trainable machine learning model is performed to obtain a derivative of the loss with respect to the number of parameters of the trainable machine learning model.

As depicted in operation 56, the number of parameters of the trainable machine learning model are updated using the loss derivatives output by operation 54 and the optimizer input from operation 48.

In one or more embodiments, the trainable machine learning model may be deep neural network and may be modified by one or more deep learning modifications (e.g., dropout, batch normalization, layer normalization, weight decay, or different choices of optimizers). In one or more embodiments, the main layer of the trainable machine learning model is an MLP mixer layer because it scales favorably with the number of atoms in a molecule. A non-limiting example of a main layer of deep neural networks that can be utilized instead of an MLP mixer layer may be a transformers layer.

Figure 1C:
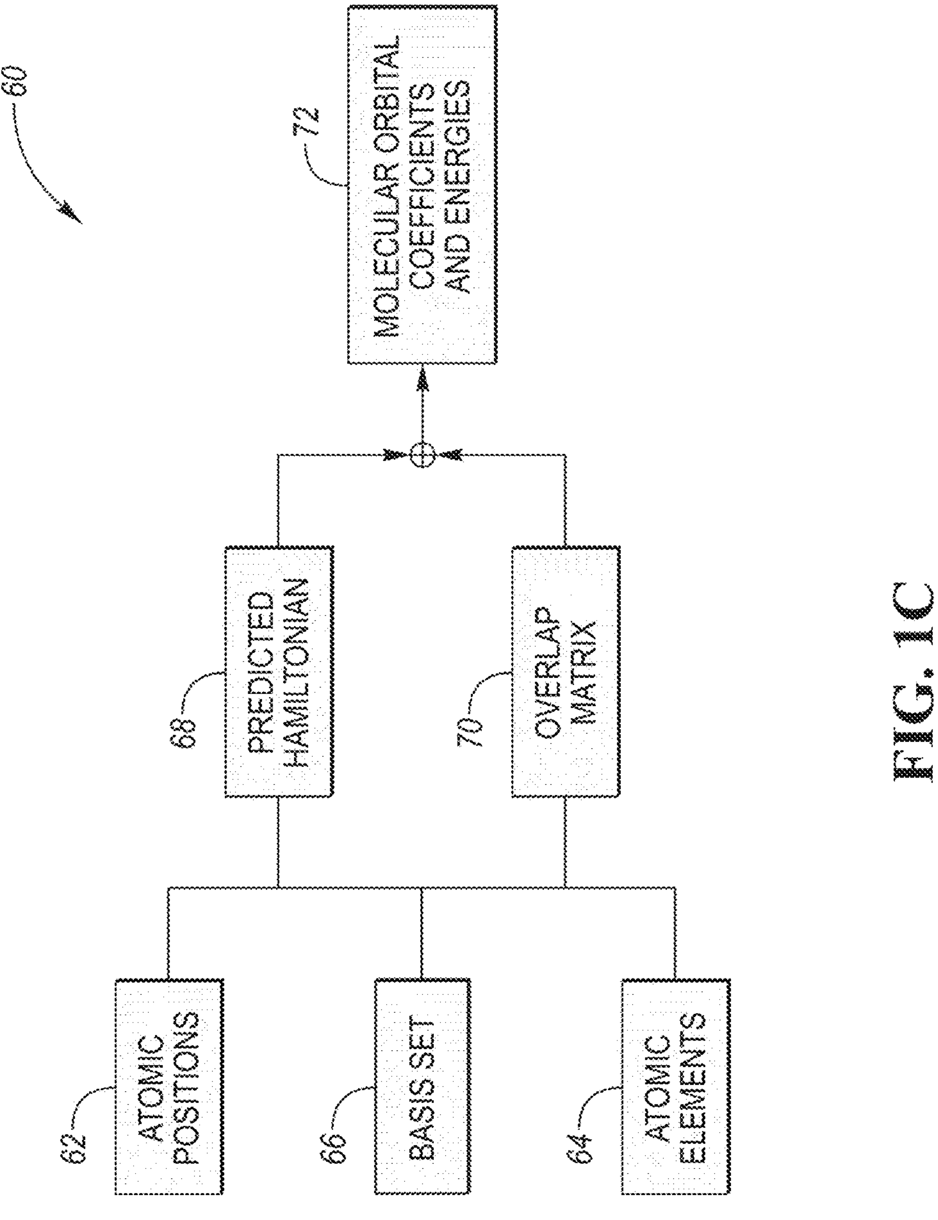
FIG. 1C depicts a flowchart of a machine learning algorithm configured to predict molecular orbital coefficients C and/or molecular orbital energies E.

FIG. 1C depicts a flowchart of machine learning algorithm 60 configured to predict molecular orbital coefficients C and/or molecular orbital energies E. FIG. 1C depicts operations 62, 64, and 66 relating to inputs of machine learning algorithm 60. Operation 62 represents an input of the atomic positions of a number of atoms in a molecule. Operation 64 represents an input of the atomic identifier (e.g., the element) of a number of atoms in the molecule. Operation 66 includes the input of a basis set including a number (e.g., a set of two or more) of rules. In one or more embodiments, the basis set is used to form a number (e.g., a set of two or more) of atomic orbitals given the atom of the molecule.

As depicted by operations 68, a forward pass is performed through a machine learning model (e.g., forward pass machine learning algorithm 10) to obtain a predicted electronic structure (e.g., a predicted Hamiltonian) of the molecule based on the inputs of operations 62, 64, and 66.

As depicted by operation 70, the forward pass of the machine learning model is performed to obtain an overlap matrix of the molecule based on the inputs of operations 62, 64, and 66.

As depicted by operation 72, molecular orbital coefficients and energies are determined based on the predicted Hamiltonian and the overlap matrix. In one or more embodiments, the predicted Hamiltonian $\hat{F}$ and the overlap matrix S are used to solve the eigenvalue problem of $\hat{F}C=SCE$ to obtain molecular orbital coefficients C and energies E of the molecule.

Figure 2:
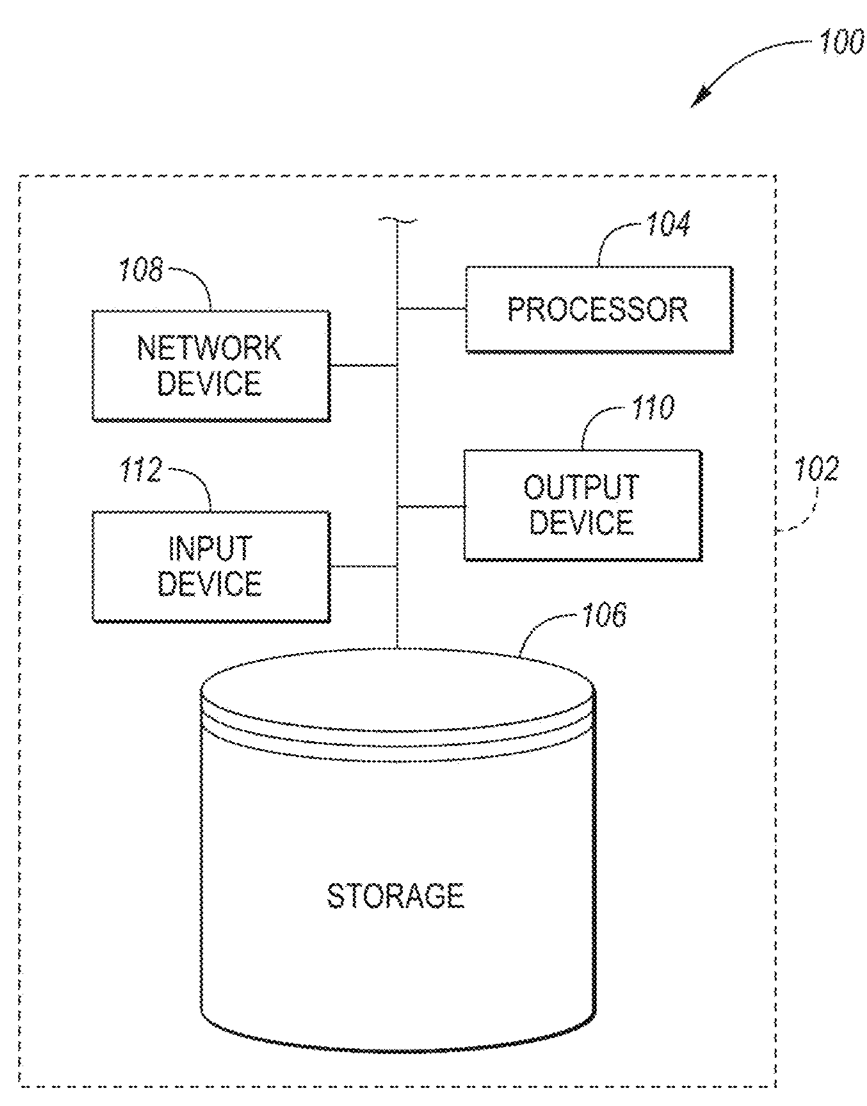
FIG. 2 illustrates a computer system including a computing device for implementing computational methods using machine learning models (e.g., trainable models) of one or more embodiments.

FIG. 2 illustrates computer system 100 including computing device 102 for implementing computational methods using machine learning models (e.g., trainable models) of one or more embodiments. Referring to FIG. 2, computing device 102 may be the hardware performing the operations set forth in FIG. 1 (e.g., a machine learning forward pass algorithm, a machine learning training algorithm as disclosed herein, and/or an algorithm for predicting molecular orbitals and coefficients. As shown, computing device 102 may include processor 104 that is operatively connected to storage 106, network device 108, output device 110, and input device 112. In other embodiments, computing device 102 may have more, fewer, or different components than shown in FIG. 2.

Processor 104 may include one or more integrated circuits that implement the functionality of a central processing unit (CPU) and/or graphics processing unit (GPU). In some examples, processors 104 are a system on a chip (SoC) that integrates the functionality of the CPU and GPU. The SoC may optionally include other components such as, for example, storage 106 and the network device 108 into a single integrated device. In other examples, the CPU and GPU are connected to each other via a peripheral connection device such as Peripheral Component Interconnect (PCI) express or another suitable peripheral data connection. In one example, the CPU is a commercially available central processing device that implements an instruction set such as one of the x86, ARM, Power, or microprocessor without interlocked pipeline stage (MIPS) instruction set families. In some examples, a neural processing unit (NPU) may be applied, e.g., if pretrained machine learning models are being used.

Regardless of the specifics, during operation processor 104 executes stored program instructions that are retrieved from storage 106. The stored program instructions, accordingly, include software that controls the operation of processors 104 to perform the operations described herein. Storage 106 may include both non-volatile memory and volatile memory devices. The non-volatile memory includes solid-state memories, such as negative-AND (NAND) flash memory, magnetic and optical storage media, or any other suitable data storage device that retains data when system 100 is deactivated or loses electrical power. The volatile memory includes static and dynamic random-access memory (RAM) that stores program instructions and data during operation of system 100.

The GPU may include hardware and software for display of at least 2D and optionally 3D graphics to output device 110. Output device 110 may include a graphical or visual display device, such as an electronic display screen, projector, printer, or any other suitable device that reproduces a graphical display. As another example, output device 110 may include an audio device, such as a loudspeaker or headphone. As yet a further example, output device 110 may include a tactile device, such as a mechanically raiseable device that may, in an example, be configured to display braille or another physical output that may be touched to provide information to a user.

Input device 112 may include any of various devices that enable the computing device 102 to receive control input from users. Examples of suitable input devices that receive human interface inputs may include keyboards, mice, track-balls, touchscreens, voice input devices, graphics tablets, and the like.

Network devices 108 may each include any of various devices that enable computing device 202 to send and/or receive data from external devices over networks. Examples of suitable network devices 208 include an Ethernet interface, a Wi-Fi transceiver, a cellular transceiver, or a BLUETOOTH or BLUETOOTH Low Energy (BLE) transceiver, or other network adapter or peripheral interconnection device that receives data from another computer or external data storage device, which can be useful for receiving large sets of data in an efficient manner.

Some existing deep learning architectures for molecular inference use exclusively basis-independent information, even when predicting basis-dependent information (e.g., the Hamiltonian F). In contrast, one or more embodiments explicitly choose a basis that the machine learning method (e.g., neural network) models, and represent each molecular configuration through basis-dependent quantities. In one or more embodiments, we use an overlap matrix S to capture geometric information together with categorical features corresponding to each atomic orbital. Elements of the overlap matrix Sij measure the spatial overlap of localized atomic orbital basis functions, and provide a detailed description of the molecular geometry specific to the choice of basis set. Unlike the Hamiltonian F, overlap matrix elements are independent of electron density, and can be quickly computed given only a choice of basis set and the atomic positions.

Though supplying the machine learning model of one or more embodiments with atomic coordinates directly as inputs provides one or more benefits. Another benefit may be providing native access to analytic derivatives with respect to the atomic positions, which may be later used for other purposes such as electronic property optimization. Another potential benefit is exposing basis set information directly as inputs to the machine learning models of one or more embodiments to provide a stronger inductive bias than basis-independent features such as atomic coordinates. As another example, the machine learning model of one or more embodiments may give a more direct link when predicting a Hamiltonian F expressed within the same basis set and carries the same symmetries as the overlap matrix S. These representations are then combined with categorical encodings of atomic orbital features that comprise the basis set. Together, the overlap matrix S and categorical atomic orbital features provide detailed geometric and basis set-specific descriptors for us to effectively predict the molecular electronic structure.

Figure 3A:
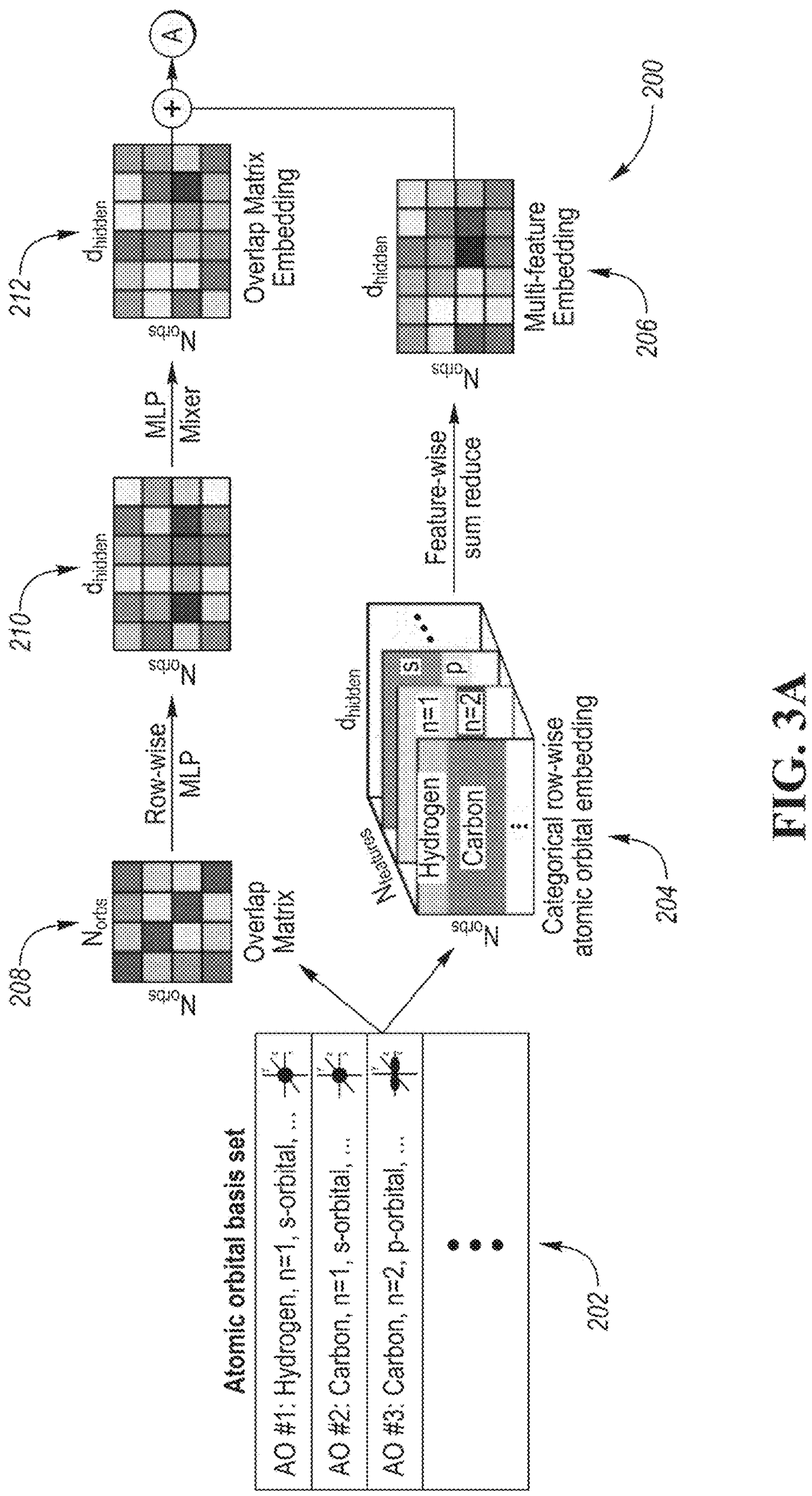
FIGS. 3A and 3B depict a schematic illustration of a deep learning architecture for predicting molecular electronic structures according to an embodiment.
Figure 3B:
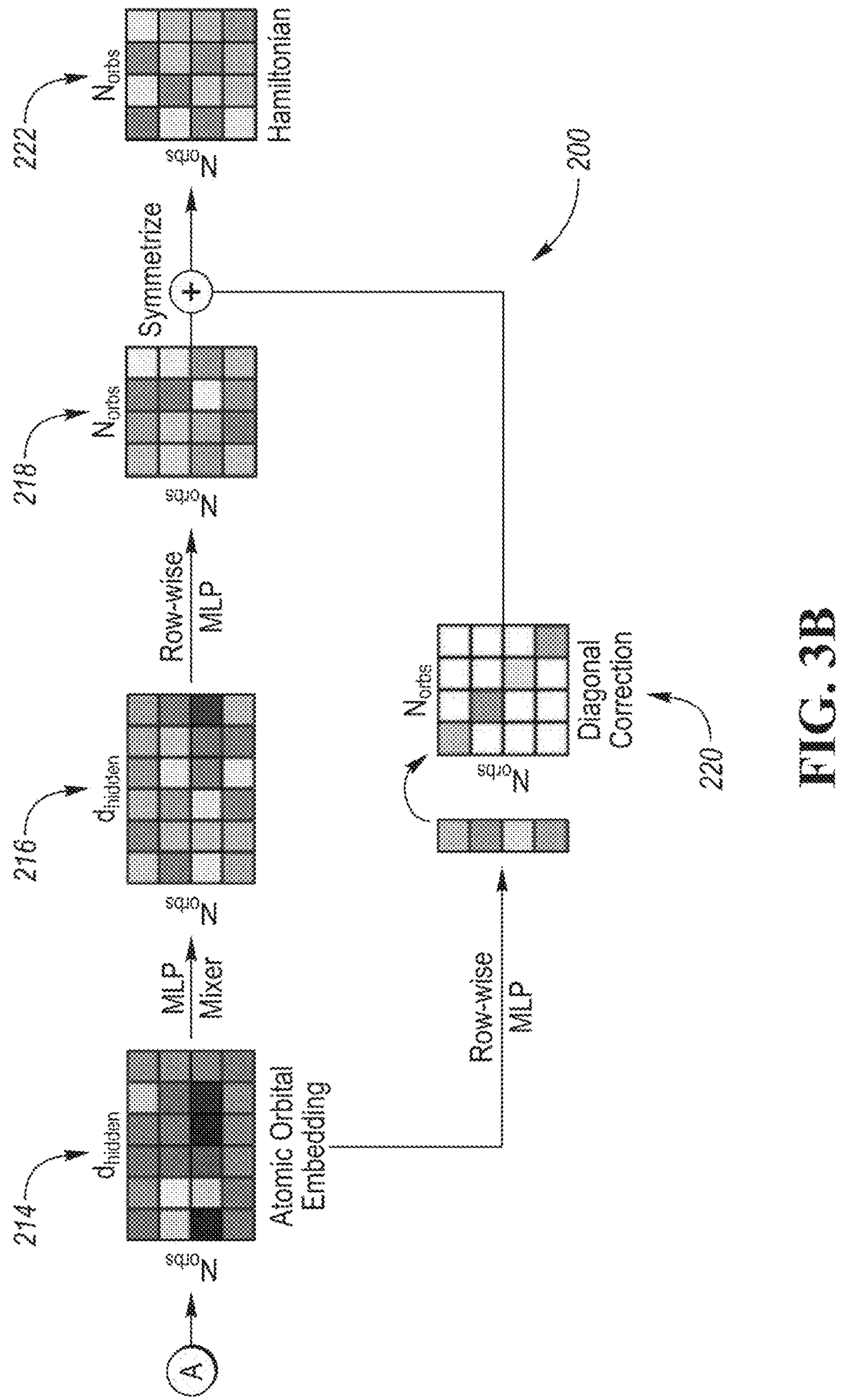

The machine learning methods of one or more embodiments present an MLP mixer-based architecture for modelling molecular electronic structure in a basis of localized atomic orbitals. FIGS. 3A and 3B depict a schematic illustration of deep learning architecture 200 for predicting molecular electronic structures according to an embodiment. The deep learning architecture 200 shown in FIGS. 3A and 3B also depicts associated data flows. The deep learning architecture 200 is configured to leverage properties of atomic orbitals that comprise DFT basis sets to predict a Hamiltonian F in the equation FC=SCE, from which molecular orbital coefficients defining electron density are derived. As depicted by block 202, a list of atomic orbitals is enumerated and comprises a set of basis functions used to model the electronic Hartree-Fock or Kohn-Sham wave-function of the system. The size and complexity of the basis set determines the achievable accuracy of the electronic structure calculation at the cost of computational expense. The size and complexity also depends on the particular system and properties of interest. Each atomic orbital may be characterized with five categorical features that uniquely specify each orbital within the basis set: (1) and (2) the index and element of the atom at which the orbital is centered, (3) the principal quantum number n, (4) the azimuthal quantum number 1, and (5) the magnetic quantum number ml. Each feature for each orbital is transformed into a $d_{hidden}$-dimensional vector (block 204) using a separate learned embedding layer (block 206) and assembled into a tensor of shape $N_{orbs}$ $d_{hidden}$ $N_{features}$. Finally performing a summation over the $N_{features}$ dimensions yields the complete multi-feature embedding for the atomic orbital basis of shape $N_{orbs}\times d_{hidden}$.

While the multi-feature embedding describes properties of each atomic orbital independent of the molecular geometry, the overlap matrix $S\in R^{N_{orbs}\times N_{orbs}}$ (block 208) provides a representation of the molecular geometry by measuring the integrable overlap of the atomic orbital functions basis which depends on the spatial arrangement of the atoms where the orbitals are localized. Each row i of S corresponds to the overlap of an atomic orbital|ϕi with the other $N_{orbs}$ orbitals. These rows are processed with an initial MLP to yield $d_{hidden}$-dimensional atomic orbital representations (block 210), and their interactions are modeled with subsequent MLP Mixer layers (block 212). As the overlap matrix S is covariant with respect to rigid rotations of the atomic coordinates, this processing step is important to capture the interdependence between the atomic orbitals and learn a globally aware overlap matrix embedding of shape $N_{orbs}\times d_{hidden}$. The multi-feature embedding is then added to this overlap matrix embedding yielding a complete atomic orbital embedding (block 214) that captures both categorical properties specific to each atomic orbital along with global spatial information of the molecular geometry.

The atomic orbital representations are further refined with another series of MLP mixers (block 216), followed by a row-wise MLP to reshape the $N_{orbs}\times d_{hidden}$ representations into the target $N_{orbs}\times N_{orbs}$ dimensionality of the Hamiltonian F (block 218). As the off-diagonal elements of the Hamiltonian $F_{i,j}$ are indicative of coupling between the atomic orbitals, the MLP mixer layer effectively captures these interactions between atomic orbitals useful for predicting the off-diagonal matrix elements. On the other hand, the diagonal elements of the Hamiltonian correspond to energies of each of the atomic orbital basis functions, and in practice are often significantly larger than their off-diagonal counterparts in magnitude. To account for these physical and numerical differences, a separate MLP row-wise is applied to the atomic orbital embeddings generating a single scalar value for each of the $N_{orbs}$ atomic orbitals (block 220). This $N_{orbs}$-dimensional vector is assembled into a diagonal matrix and added to the $N_{orbs}\times N_{orbs}$ dimensional output of the interaction branch, constituting a diagonal correction to the interaction branch and providing an inductive bias delineating the on- and off-diagonal elements of the Hamiltonian F. As the Hamiltonian F is always symmetric, the diagonally corrected representations $\tilde{F}$ are symmetrized to obtain the complete predicted Hamiltonian $$F=\frac{1}{2}\left(\tilde{F}+\tilde{F}^{T}\right)$$

(block 222). From the predicted Hamiltonian F, the molecular orbital coefficients, energies and electron density are obtained by solving FC=SCE, giving access to the molecular electronic structure and a plethora of chemical and physical properties for the system.

The machine learning models of one or more embodiments may be trained end-to-end using mini-batch stochastic gradient descent and an ADAM optimizer using a simple mean squared error (MSE) between the true $F^{(true)}$ and predicted $F^{(pred)}$ Hamiltonians as represented by equation (1) below.

$$L\left(F^{(true)}, F^{(pred)}\right) = \frac{1}{N_{orbs}^2}\left\|F^{(true)} - F^{(pred)}\right\|_F^2 \tag{1}$$

Both the input overlap matrix S and the Hamiltonian F are covariant with respect to rigid rotations of the atomic coordinates represented by equation (2) below.

$$r \in \mathbb{R}^{N_{atoms} \times 3} \tag{2}$$

Data augmentation is performed so that the machine learning model learns this covariance where during training a random rotation matrix R performs a rigid rotation of the atomic coordinates $r'=rR^T$ for each training sample. The corresponding covariant change to the overlap S and the Hamiltonian F matrices due to this rigid rotation R is then accounted for using Wigner rotation matrices as represented by equation (3) below.

$$\mathcal{D}_R \in \mathbb{R}^{N_{orbs} \times N_{orbs}} \tag{3}$$

via a unitary transformation as represented by equation (4) below.

$$S' = \mathcal{D}_R^T S \mathcal{D}_R \tag{4}$$

$$F' = D_R^T F \mathcal{D}_R.$$

During training, a separately maintained exponential moving average of the model parameters may be used at an inference time, as this may lead to improved generalizability. The machine learning system of one or more embodiments may contains about 38 million parameters, which is about 2.5 fewer than the about 93M parameters in the SchNOrb architecture, but about 2 more than the about 17M parameters of the PhiSNet model.

The neural network of one or more embodiments is configured to accurately predict the Hamiltonian F used to determine the electronic density and other derivable physical and chemical properties for a variety of molecular systems.

The orbital mixer model is evaluated against the SchNOrb model and the PhiSNet model on three separate molecular configuration datasets. Similar to the SchNOrb model, but unlike the PhiSNet model, the orbital mixer model is not explicitly covariant with respect to rigid molecular rotations but rather is trained using data augmentation to learn this equivariance, although explicitly covariant schemes can also be developed. Improved accuracy and data and parameter efficiency is reported when predicting the electronic Hamiltonian F, molecular orbital coefficients and energies compared to the SchOrb model while also performing competitively compared to the PhiSNet model. Integrating the orbital mixer model into quantum chemistry workflows using the predicted Hamiltonian F as an initial guess to DFT calculations achieves improved convergence speeds compared to conventional methods. Directly predicting the electronic structure gives us access to a variety of derivable physical chemical properties without needing to train separate machine learning models for each property of interest. Agreement between the orbital mixer predicted and reference calculations for HOMO-LUMO gap energies and electronic dipole moments is shown. The orbital mixer architecture of one or more embodiments benefits from simple and intuitive construction while leveraging strong inductive biases operating directly on atomic orbital representations to achieve competitive prediction accuracies.

As shown below, the neural network of one or more embodiments is evaluated on conformational geometries of small molecule molecular dynamics trajectories taken from an MD17 dataset (e.g., ethanol, malondialdehyde, and uracil). While the MD17 dataset natively contains only energy and force labels, the dataset used in one or more embodiments is curated by performing reference DFT calculations using the PySCF quantum chemistry code on the same subset of 30,000 MD17 molecular configurations for each molecule used in the SchNOrb and PhiSNet models. In one or more embodiments, separate neural networks are trained for each molecule at two different training set sizes of 25K and 950 configurations alongside comparisons to results from the SchNOrb and PhiSNet models.

Numerical results of the disclosed neural network's performance (referred to as the orbital mixer model) to the SchNOrb and PhiSNet models are presented in Table 1 below. Table 1 includes a comparison of Hamiltonian F, occupied molecular orbital (MO) energies and MO coefficient prediction accuracies between the orbital mixer, SchNOrb, and PhiSNet models for the three test molecules of ethanol, malondialdehyde, and uracil. Comparisons are generated using two different training set sizes of 950 and 25K configurations for both the orbital mixer and SchNOrb models and compare to the reported results at 25K training samples for the PhiSNet2 model. Reported PhiSNet cosine similarities are rounded to fewer significant digits than reported in Table 1. Results for PhiSNet are taken from Unke, O. T., Chmiela, S., Sauceda, H. E., Gastegger, M., Poltaysky, I., Schutt, K. T., Tkatchenko, A., and Muller, K.-R. Machine learning force fields. Chemical Reviews, 2021c. The SchNOrb models are trained in this work using the publicly available implementation at https://github.com/atomistic-machine-learning/SchNOrb.

TABLE 1

| Molecule | Model (train size) | Hamiltonian MAE [eV] | MO energy MAE [eV] | MO coefficient cosine similarity |
|---|---|---|---|---|
| Ethanol | Orbital mixer (25K) | 0.0020 | 0.0037 | 0.9999 |
| | PhiSNet (25K) | 0.00033 | 0.0017 | 1.00 |
| | SchNOrb (25K) | 0.0052 | 0.0084 | 0.9978 |
| | Orbital mixer (950) | 0.0026 | 0.0054 | 0.9998 |
| | SchNOrb (950) | 0.0074 | 0.0130 | 0.9941 |
| Malondialdehyde | Orbital mixer (25K) | 0.0021 | 0.0046 | 0.9984 |
| | PhiSNet (25K) | 0.00034 | 0.0020 | 1.00 |
| | SchNOrb (25K) | 0.0052 | 0.0117 | 0.9866 |
| | Orbital mixer (950) | 0.0029 | 0.0064 | 0.9973 |
| | SchNOrb (950) | 0.0075 | 0.0221 | 0.9661 |
| Uracil | Orbital mixer (25K) | 0.0025 | 0.0059 | 0.9965 |
| | PhiSNet (25K) | 0.00029 | 0.0023 | 1.00 |
| | SchNOrb (25K) | 0.0064 | 0.0355 | 0.9269 |
| | Orbital mixer (950) | 0.0030 | 0.0074 | 0.9941 |
| | SchNOrb (950) | 0.0086 | 0.1550 | 0.8003 |

For each tested molecule and training size, the disclosed neural network outperforms the SchNOrb model and achieves mean absolute errors (MAEs) below 0.003 eV on all Hamiltonian predictions. The disclosed neural network trained on only 950 configurations for each test molecule generates more accurate Hamiltonian F MAE predictions than the SchNOrb model trained with 25K configurations. A significant improvement is demonstrated compared to the SchNOrb model when training on the relatively largest and most challenging molecule, uracil, which is modeled in a basis set of 132 atomic orbitals (29 occupied plus 103 virtual). Compared to a SchNOrb model trained with 25K samples, the disclosed neural network achieves 53% improvement when trained with 950 samples and 61% improvement when trained with 25K samples on uracil. The disclosed neural network achieves impressive accuracy on occupied molecular orbital (MO) energy and coefficient prediction, outperforming the SchNOrb model on these metrics while predicting MO energies to within 0.0075 eV MAE and MO coefficients to greater than 99% cosine similarity for all test molecules and training set sizes.

Figure 4A:
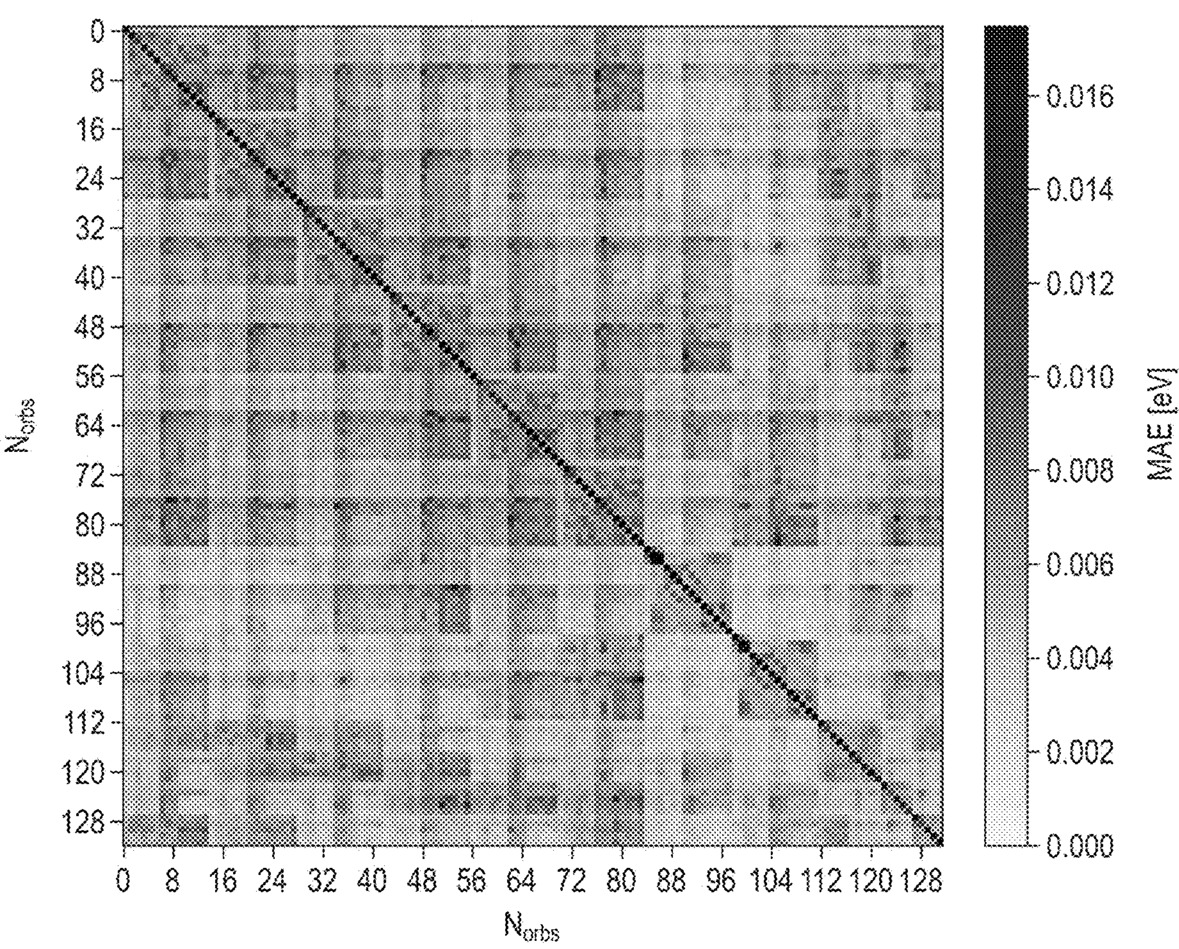
FIGS. 4A through 4L presents a detailed comparison of Hamiltonian F and MO coefficients and energies predictions generated by the orbital mixer neural network trained with 950 configurations and the SchNOrb model trained with 25K configurations for uracil.
Figure 4B:
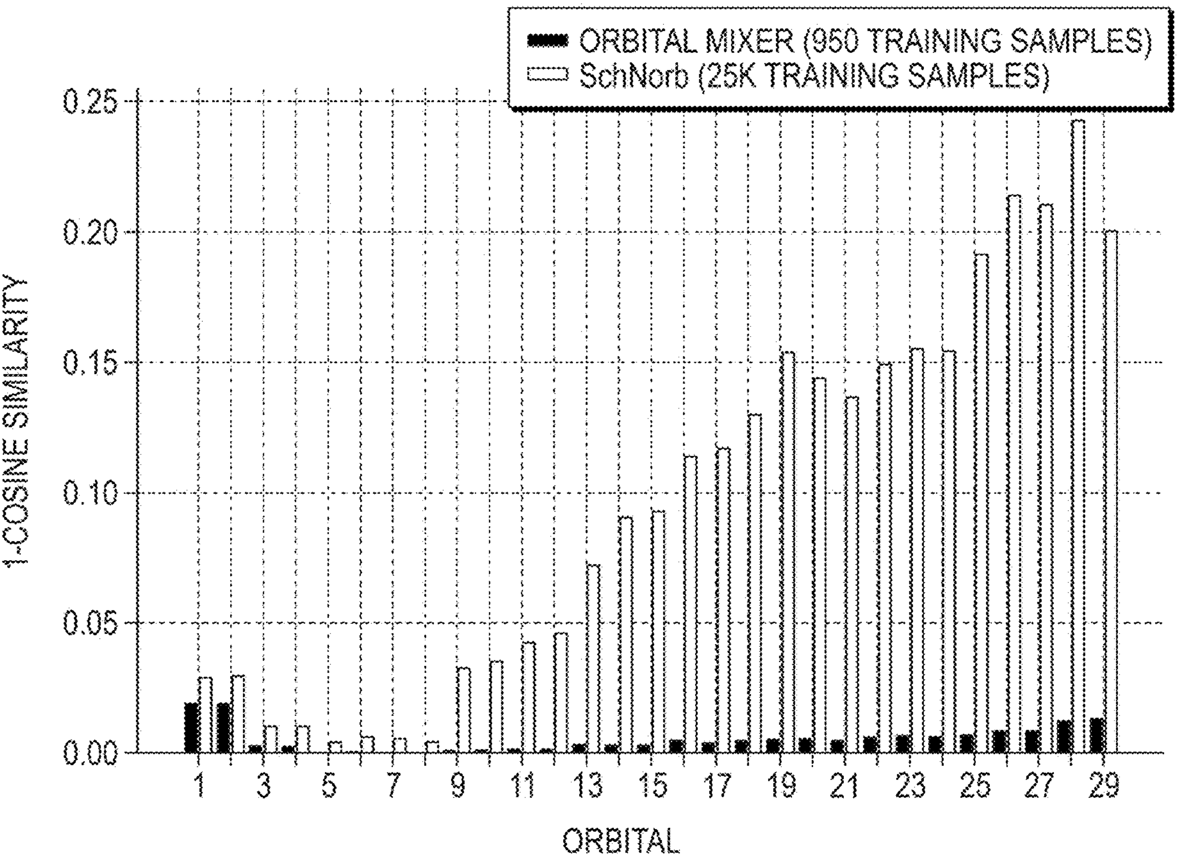
Figure 4C:
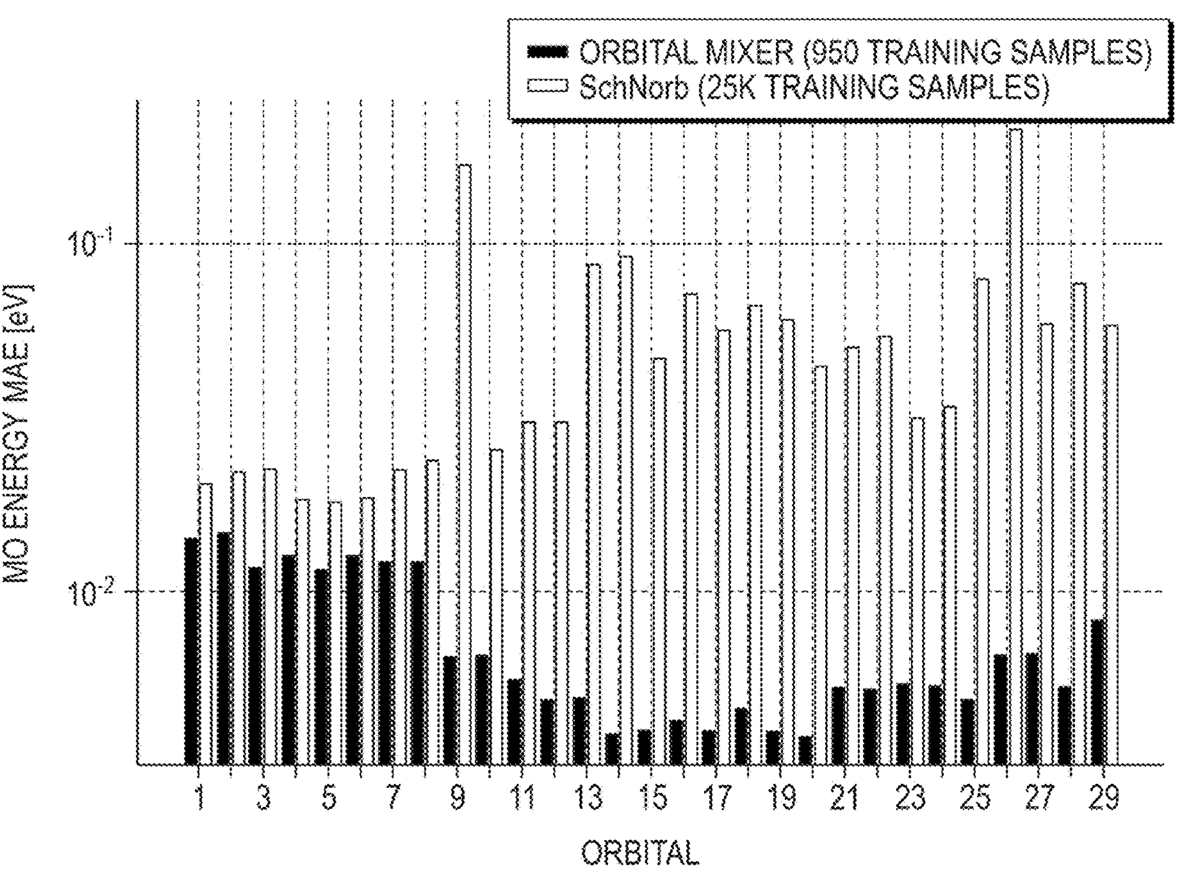
Figure 4D:
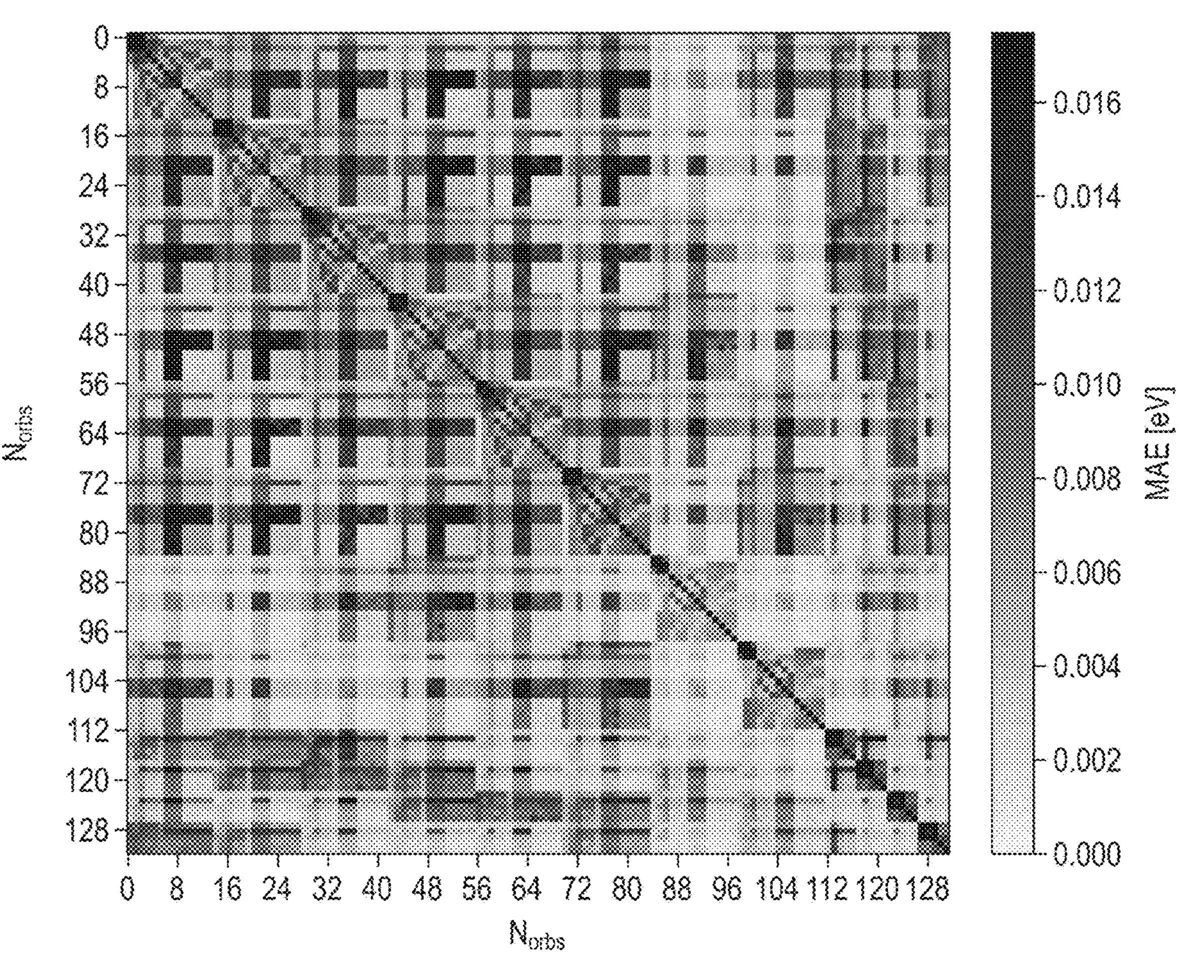
Figure 4E:
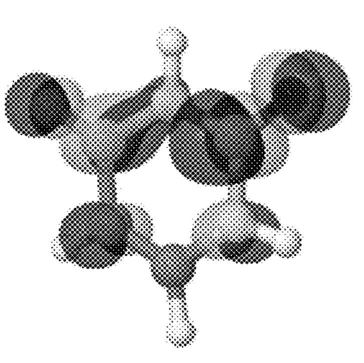
Figure 4F:
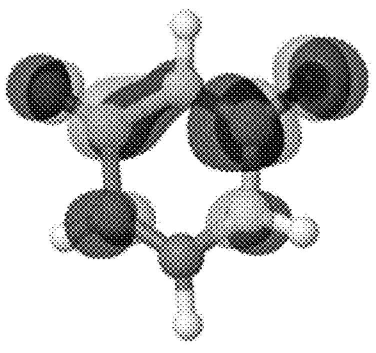
Figure 4G:
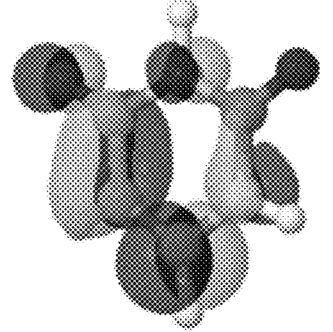
Figure 4H:
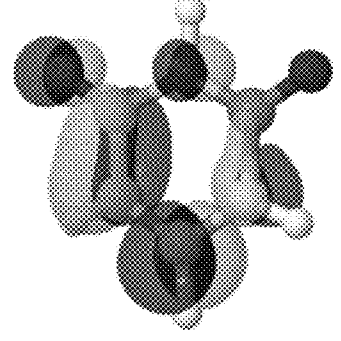
Figure 4I:
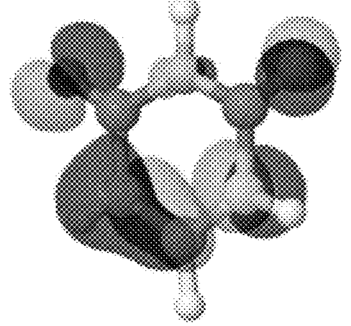
Figure 4J:
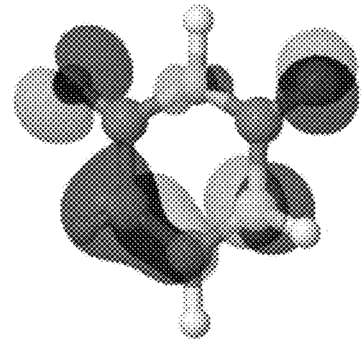
Figure 4K:
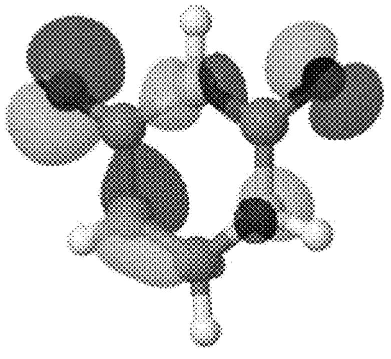
Figure 4L:
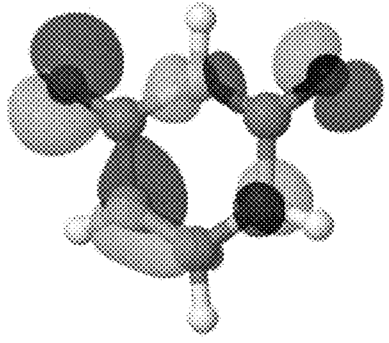

FIGS. 4A through 4L presents a detailed comparison of Hamiltonian F and MO coefficients and energies predictions generated by the orbital mixer neural network trained with 950 configurations and the SchNOrb model trained with 25K configurations for uracil. FIG. 4A depicts a matrix element-wise test set MAE of the predicted uracil Hamiltonian F using 950 training samples of the orbital mixer neural network. FIG. 4D depicts a matrix element-wise test set MAE of the predicts uracil Hamiltonian F using 25K training samples of the SchNOrb model. Beyond the concentration of both models' prediction errors along the diagonal (as expected, due to the diagonal entries' significantly larger magnitude), The SchNOrb model predictions produce significantly larger errors in select off-diagonal blocks, while errors from the orbital mixer predictions are comparatively lower throughout the off-diagonal elements. FIG. 4B demonstrates cosine similarity between the SchNOrb model and the orbital mixer predicted MO coefficients delineated for the 29 occupied orbitals of uracil. The orbital mixer model does not perform worse than about 0.983 cosine similarity for any occupied orbital, while the SchNOrb model only performs better than the orbital mixer model's worst performer for 6 out of 29 occupied orbitals. FIG. 4C demonstrates that the MAE between the ground truth and predicted occupied MO energies for both the orbital mixer and SchNOrb model. The largest error orbital of the orbital mixer model (orbital 2 at about 0.012 eV) performs better than all the predicted SchNOrb orbitals and about 52% better than the best SchNOrb orbital. The orbital mixer model achieves these prediction accuracies using about 10 fewer training samples than the SchNOrb model.

FIGS. 4E through 4L depict the shapes of the frontier molecular orbitals for a fixed uracil configuration derived from both the orbital mixer predicted and the ground truth MO coefficients. FIGS. 41, 4G, 4K, and 4E depict the orbital shapes of the orbital mixer predicted for the highest occupied molecular orbital (HOMO), the lowest unoccupied molecular orbital (LUMO) and the two nearby occupied (HOMO-1) and unoccupied (LUMO+1) molecular orbitals, respectively. FIGS. 4J, 4H, 4L, and 4F depict the orbital shapes of the ground truth MO coefficients for HOMO, LUMO, HOMO-1, and LUMO+1, respectively.

Figure 5A:
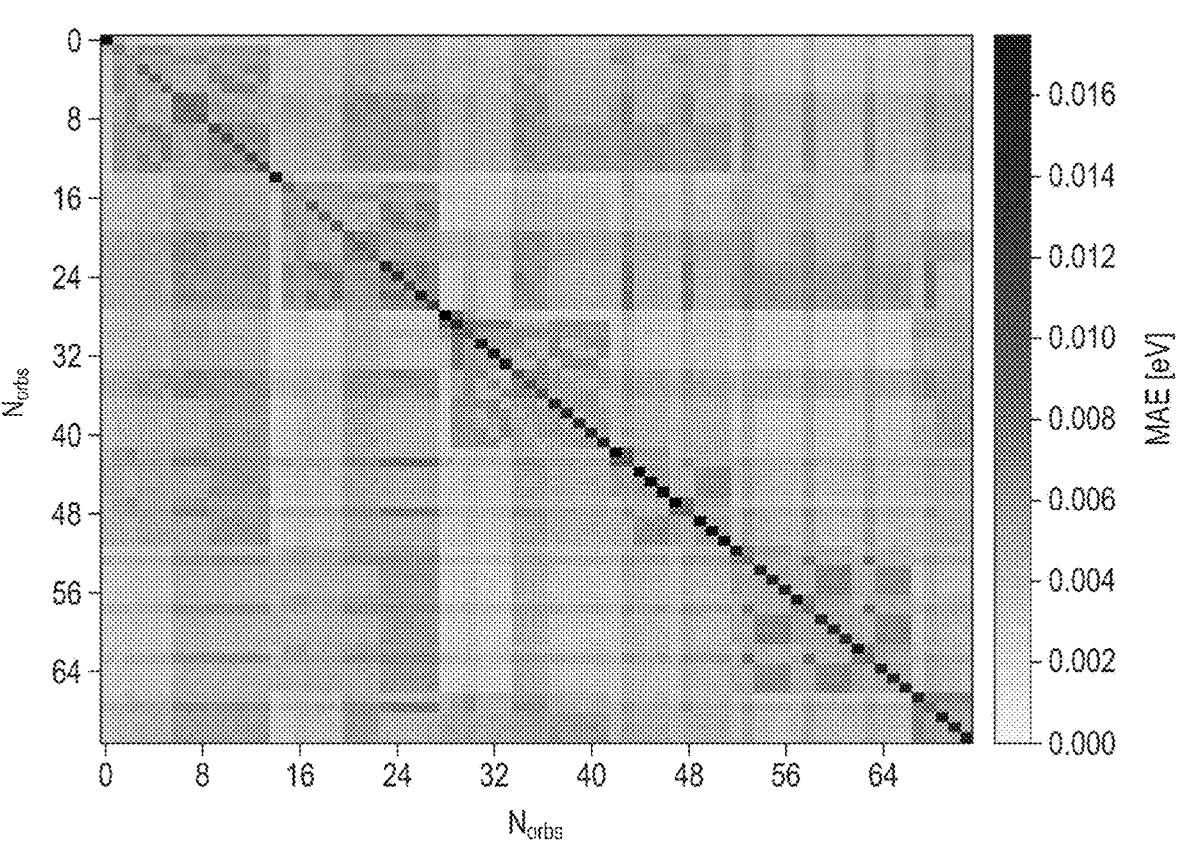
FIGS. 5A through 5L presents a detailed comparison of Hamiltonian F and MO coefficients and energies predictions generated by the orbital mixer neural network trained with 950 configurations and the SchNOrb model trained with 25K configurations for ethanol.
Figure 5B:
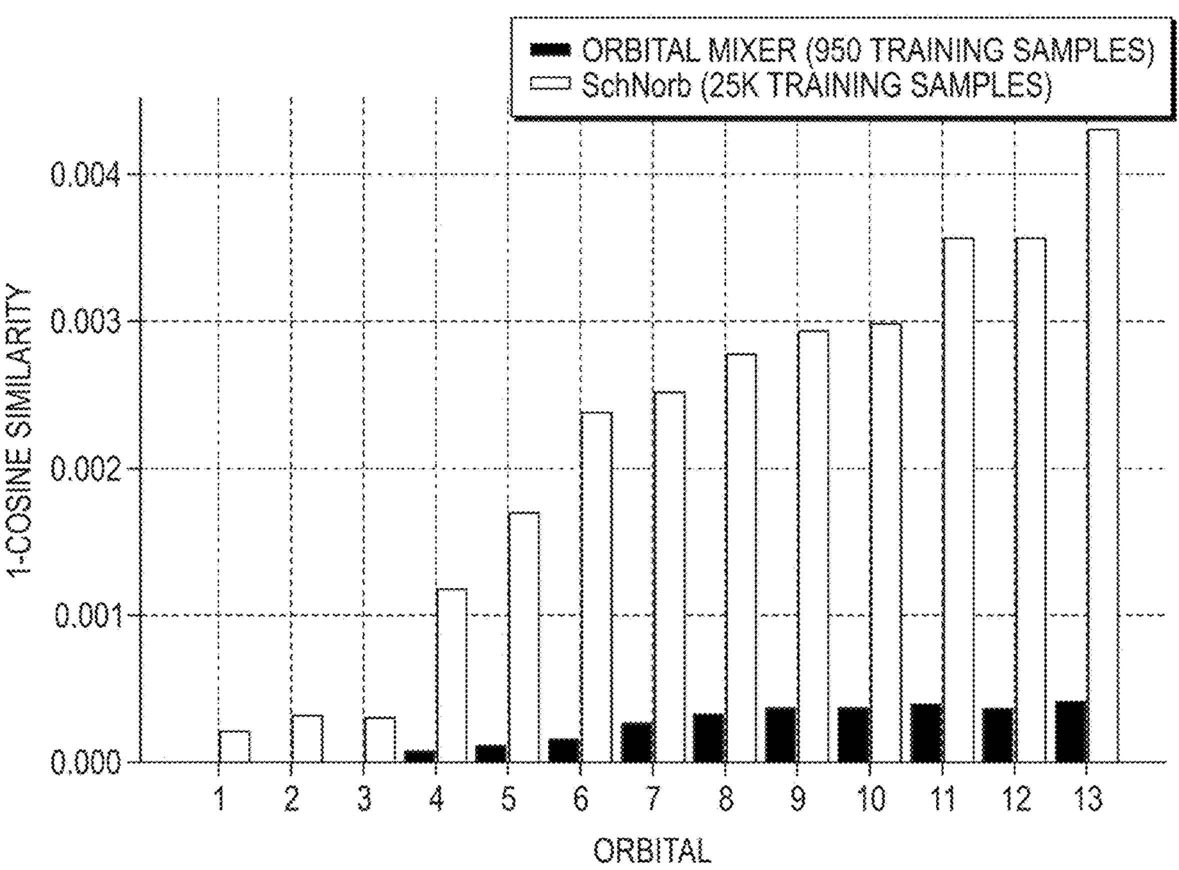
Figure 5C:
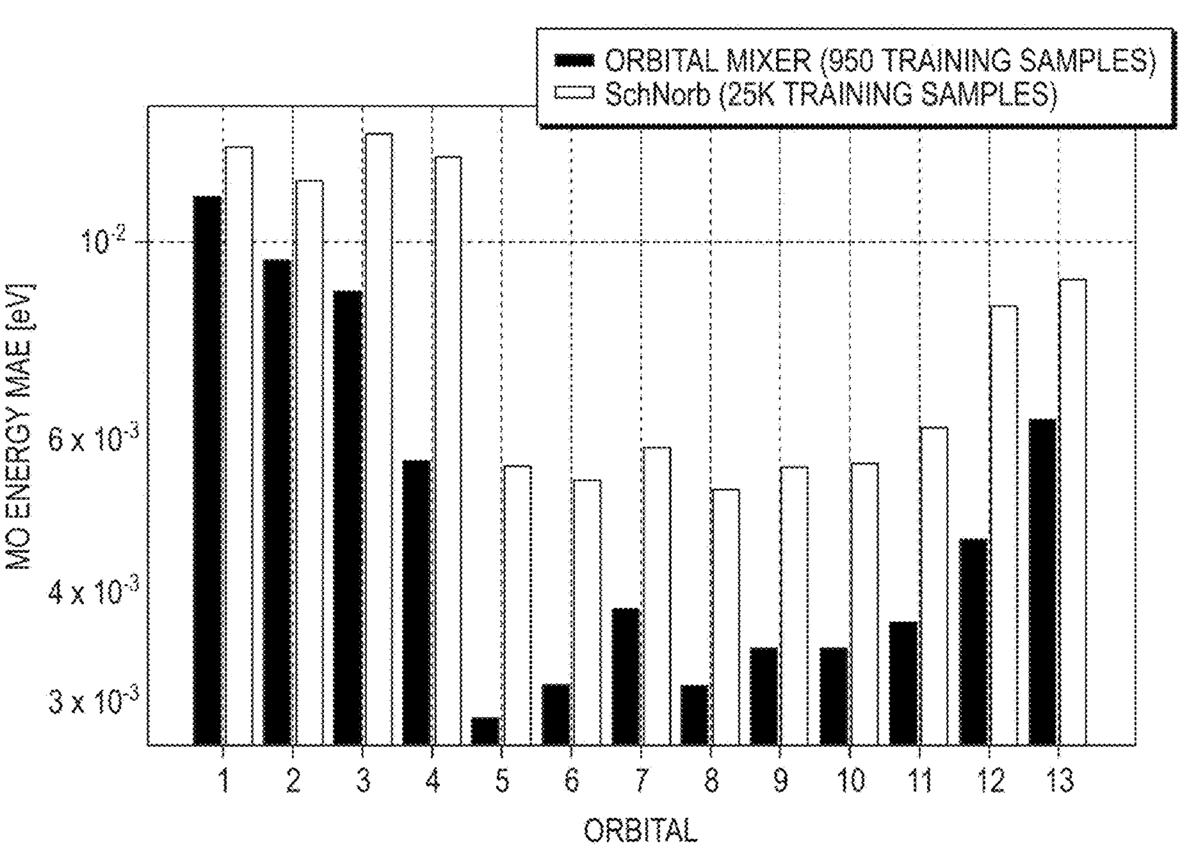
Figure 5D:
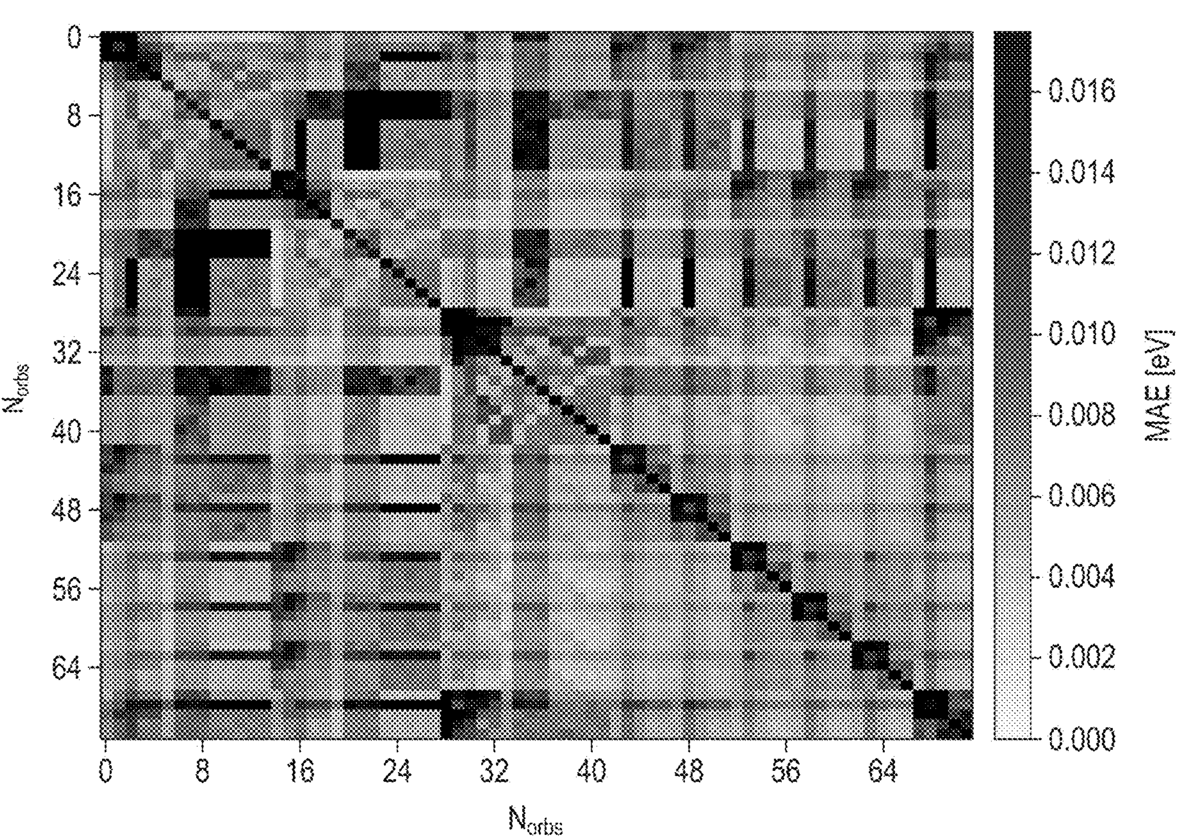
Figure 5E:
Figure 5F:
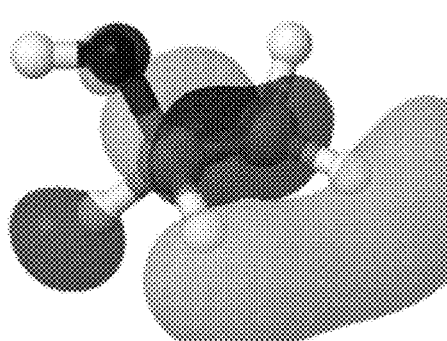
Figure 5F:
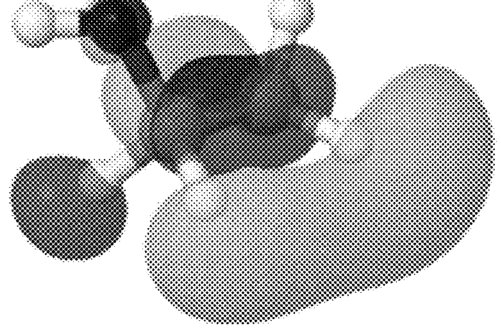
Figure 5G:
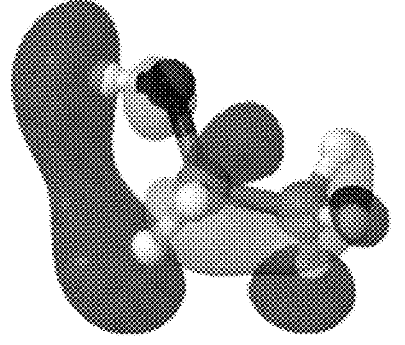
Figure 5H:
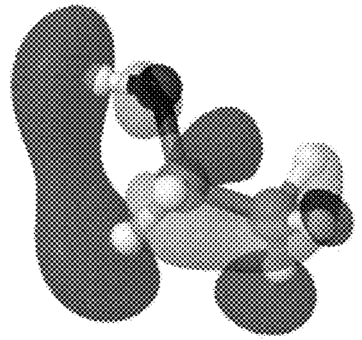
Figure 5I:
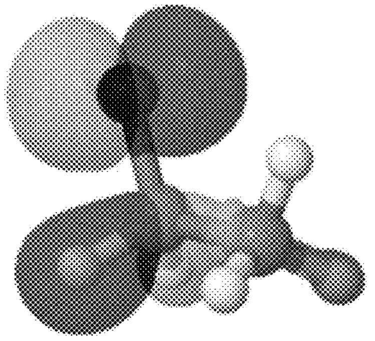
Figure 5J:
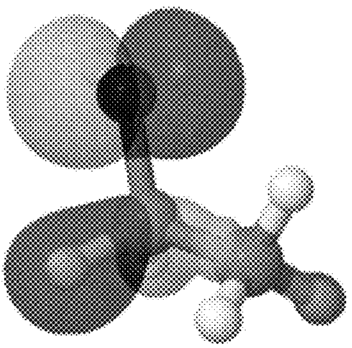
Figure 5K:
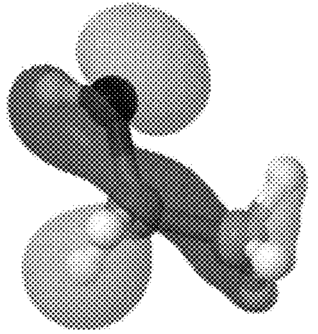
Figure 5L:
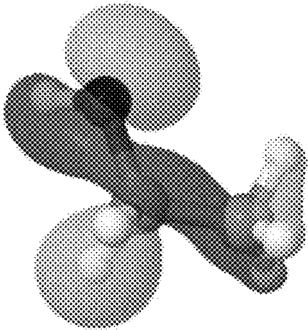

FIGS. 5A through 5L presents a detailed comparison of Hamiltonian F and MO coefficients and energies predictions generated by the orbital mixer neural network trained with 950 configurations and the SchNOrb models trained with 25K configurations for ethanol. FIG. 5A depicts a matrix element-wise test set MAE of the predicted ethanol Hamiltonian F using 950 training samples of the orbital mixer neural network. FIG. 5D depicts a matrix element-wise test set MAE of the predicts ethanol Hamiltonian F using 25K training samples of the SchNOrb model. FIG. 5B demonstrates cosine similarity between the SchNOrb and orbital mixer predicted MO coefficients delineated for the 13 occupied orbitals of ethanol. FIG. 5C demonstrates that the MAE between the ground truth and predicted occupied MO energies for both the orbital mixer and SchNOrb models.

FIGS. 5E through 5L depict the shapes of the frontier molecular orbitals for a fixed ethanol configuration derived from both orbital mixer predicted and ground truth MO coefficients. FIGS. 51, 5G, 5K, and 5E depict the orbital shapes of the orbital mixer predicted for the highest occupied molecular orbital (HOMO), the lowest unoccupied molecular orbital (LUMO) and the two nearby occupied (HOMO-1) and unoccupied (LUMO+1) molecular orbitals, respectively. FIGS. 5J, 5H, 5L, and 5F depict the orbital shapes of the ground truth MO coefficients for HOMO, LUMO, HOMO-1, and LUMO+1, respectively.

Figure 6A:
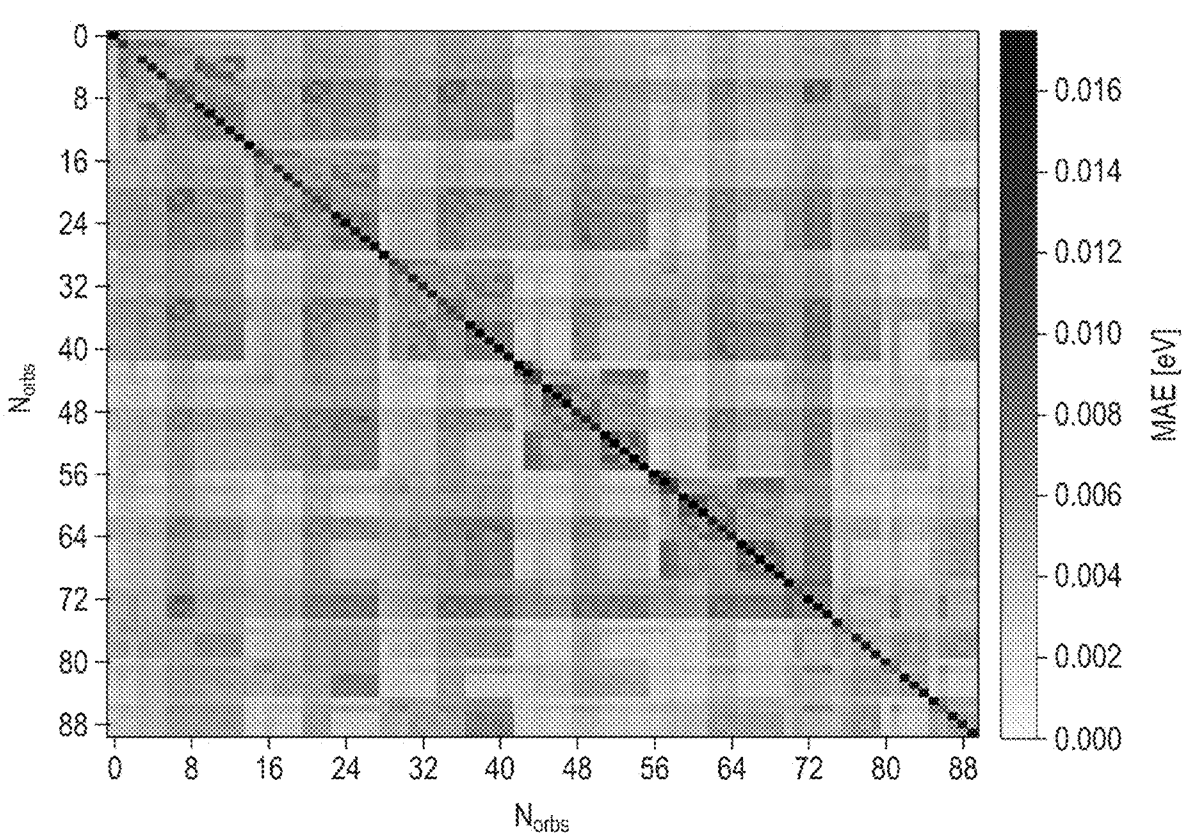
FIGS. 6A through 6L presents a detailed comparison of Hamiltonian F and MO coefficients and energies predictions generated by the orbital mixer neural network trained with 950 configurations and the SchNOrb model trained with 25K configurations for malondialdehyde.
Figure 6B:
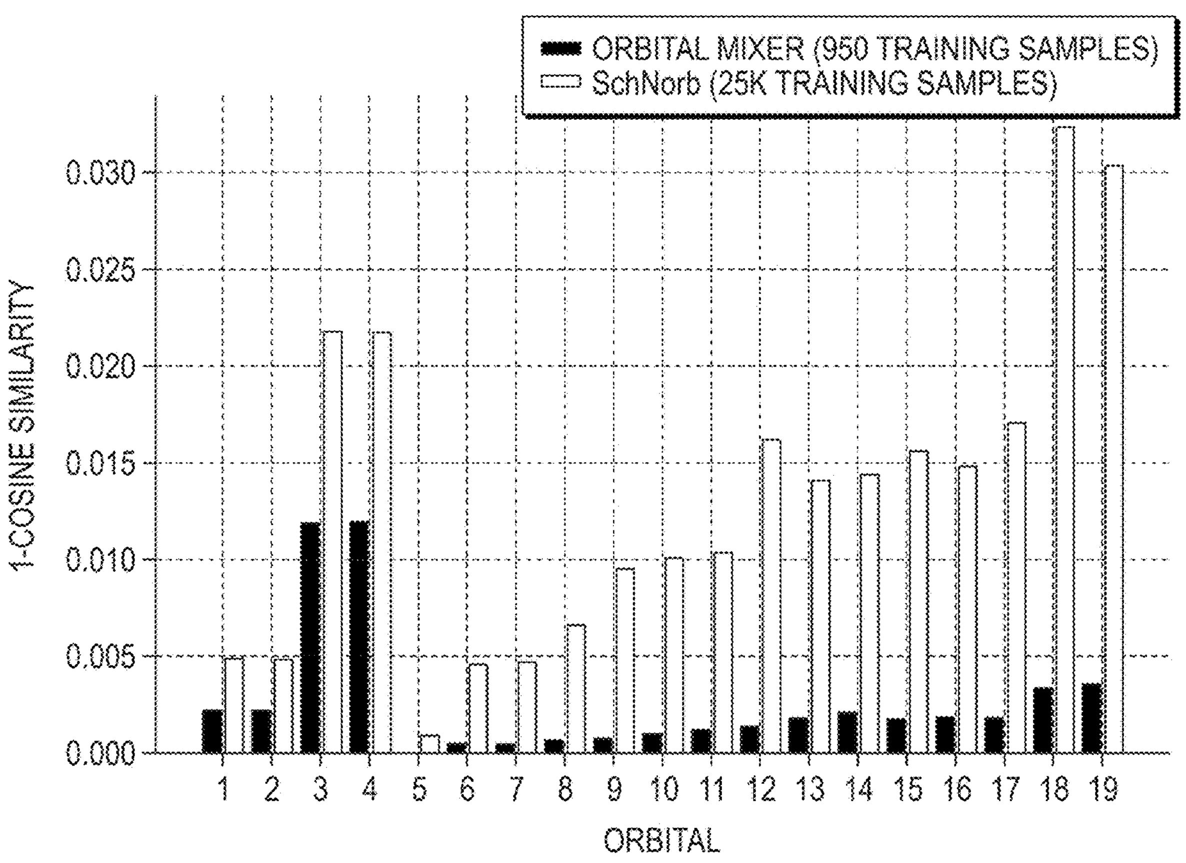
Figure 6C:
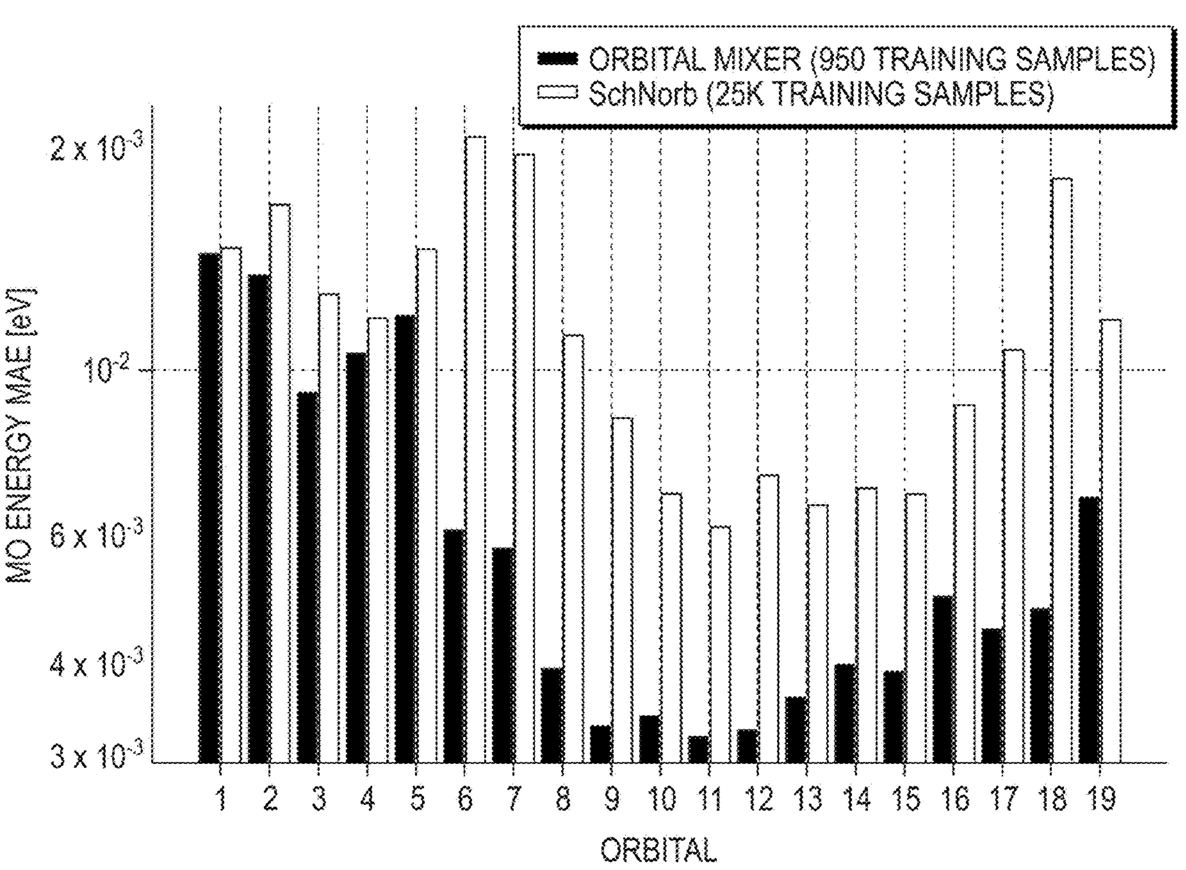
Figure 6D:
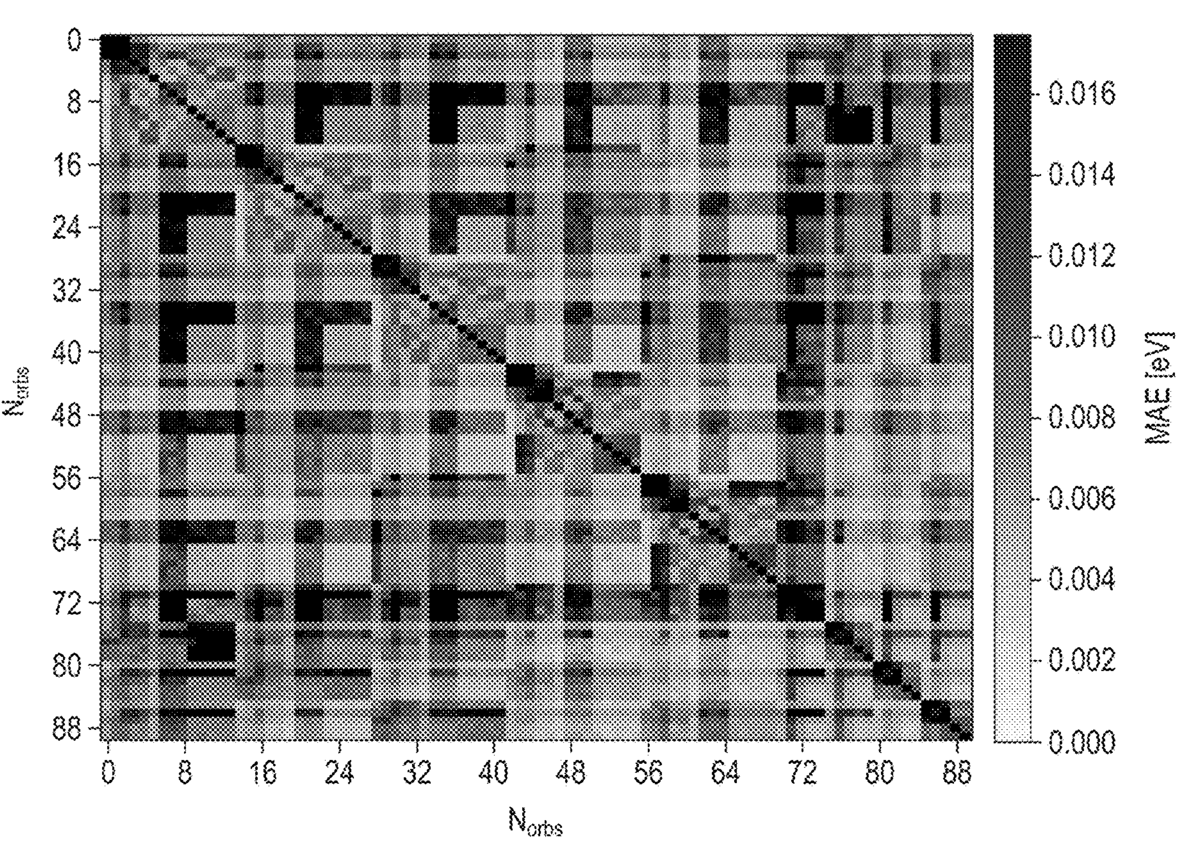
Figure 6E:
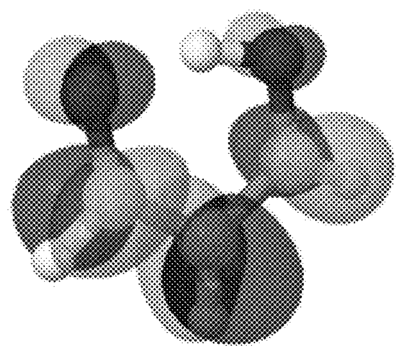
Figure 6F:
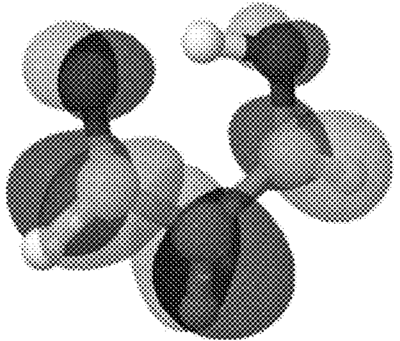
Figure 6G:
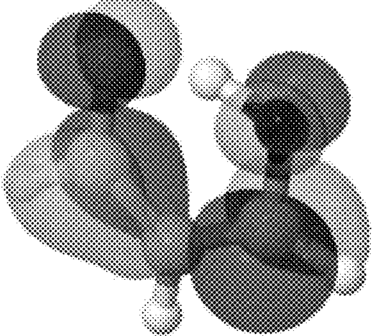
Figure 6H:
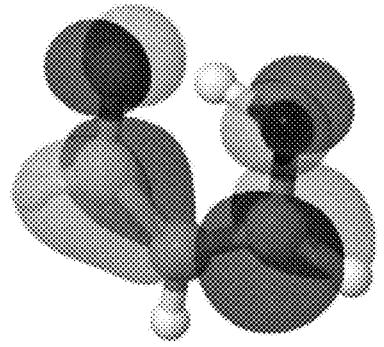
Figure 6I:
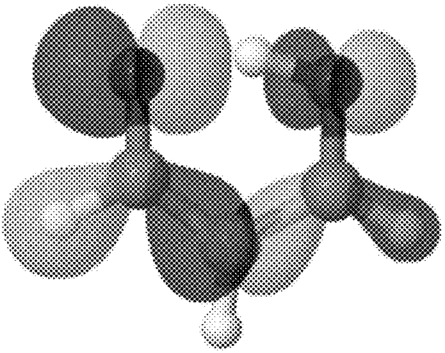
Figure 6J:
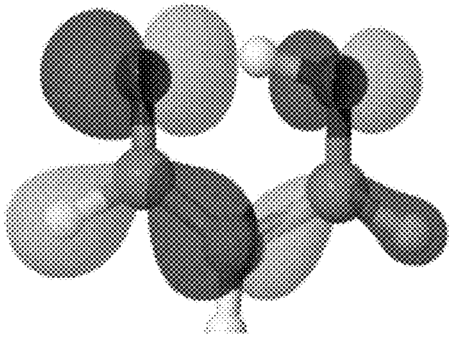
Figure 6K:
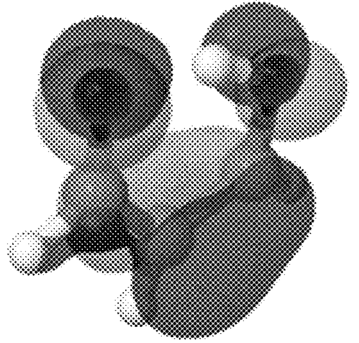
Figure 6L:
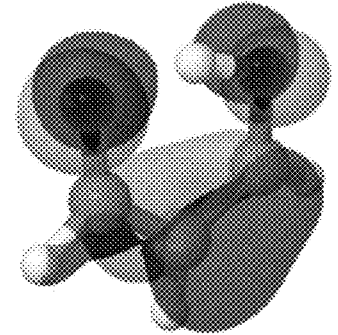

FIGS. 6A through 6L presents a detailed comparison of Hamiltonian F and MO coefficients and energies predictions generated by the orbital mixer neural network trained with 950 configurations and the SchNOrb model trained with 25K configurations for malondialdehyde. FIG. 6A depicts a matrix element-wise test set MAE of the predicted malondialdehyde Hamiltonian Fusing 950 training samples of the orbital mixer neural network. FIG. 6D depicts a matrix element-wise test set MAE of the predicts malondialdehyde Hamiltonian F using 25K training samples of the SchNOrb model. FIG. 6B demonstrates cosine similarity between the SchNOrb and the orbital mixer predicted MO coefficients delineated for the 13 occupied orbitals of malondialdehyde. FIG. 6C demonstrates that the MAE between the ground truth and predicted occupied MO energies for both the orbital mixer and SchNOrb models.

FIGS. 6E through 6L depict the shapes of the frontier molecular orbitals for a fixed malondialdehyde configuration derived from both the orbital mixer predicted and the ground truth MO coefficients. FIGS. 6I, 6G, 6K, and 6E depict the orbital shapes of the orbital mixer predicted for the highest occupied molecular orbital (HOMO), the lowest unoccupied molecular orbital (LUMO) and the two nearby occupied (HOMO-1) and unoccupied (LUMO+1) molecular orbitals, respectively. FIGS. 6J, 6H, 6L, and 6F depict the orbital shapes of the ground truth MO coefficients for HOMO, LUMO, HOMO-1, and LUMO+1, respectively.

The capability to accurately predict the Hamiltonian F of one or more embodiments for a molecular system enables integration of the orbital mixer model with electronic structure calculations. The Hamiltonian predictions generated by an orbital mixer model can be used as initial guess in the equation represented by FC=SCE, which is then solved using the self-consistent field (SCF) method to arrive at a converged estimate of the Hamiltonian F, and therefore the electron density. The speed of these DFT calculations is in large part determined by the number SCF iterations required to reach convergence. High quality initial guesses for the Hamiltonian F may greatly expedite the SCF procedure and enable higher-throughput DFT calculations. We perform experiments testing speed-up with respect to number of SCF iterations by initializing DFT calculations using the orbital mixer predicted Hamiltonian F.

Figures 7A, 7B:
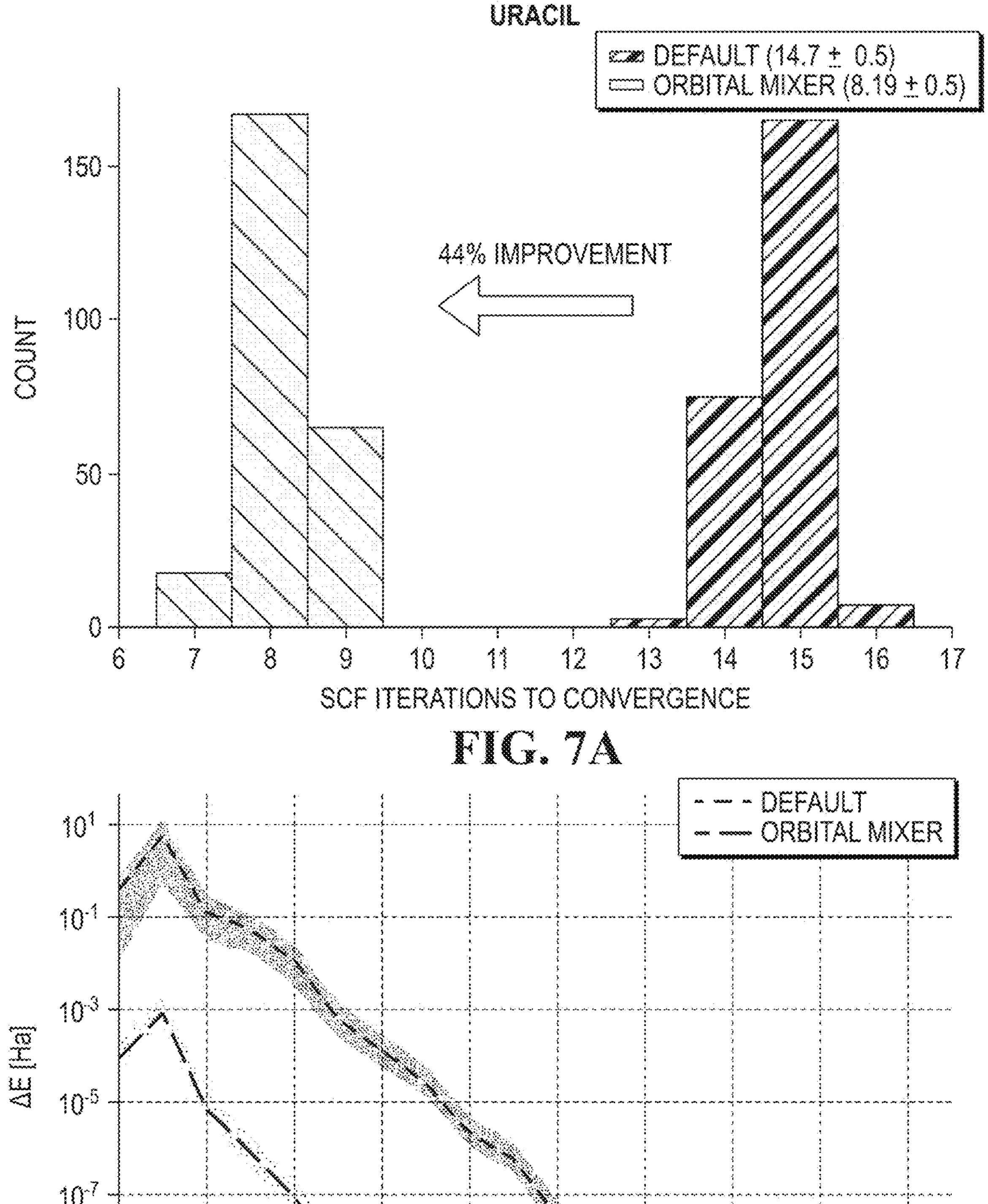
FIG. 7A is a graph that reports a distribution of self-consistent field (SCF) iterations to convergence for DFT calculations performed on 250 test set uracil configurations using both the default PySCF model and the orbital mixer model predicted Hamiltonian F for initialization.
FIG. 7B is a graph that tracks the difference in the total energy estimated after each SCF iteration as compared to the terminal converged energy estimate for uracil.

FIG. 7A is a graph that reports a distribution of self-consistent field (SCF) iterations to convergence for DFT calculations performed on 250 test set uracil configurations using both the default PySCF model and the orbital mixer model predicted Hamiltonian F for initialization. The orbital mixer initialization achieves a 44% improvement in the number of SCF iterations required to reach convergence compared to the default PySCF initialization strategy. FIG. 7B is a graph that tracks the difference in the total energy estimated after each SCF iteration as compared to the terminal converged energy estimate for uracil. Although both initialization schemes eventually reach the same energy difference criterion of $10^{-9}$ Ha, all configurations using the orbital mixer initialization reliably converge after only at most 9 SCF iterations. In similar SCF initialization experiments, the SchNorb model reports a speedup of 15% and the PhiSNet model reports a speedup of 47% SCF iterations for uracil.

Figures 8A, 8B:
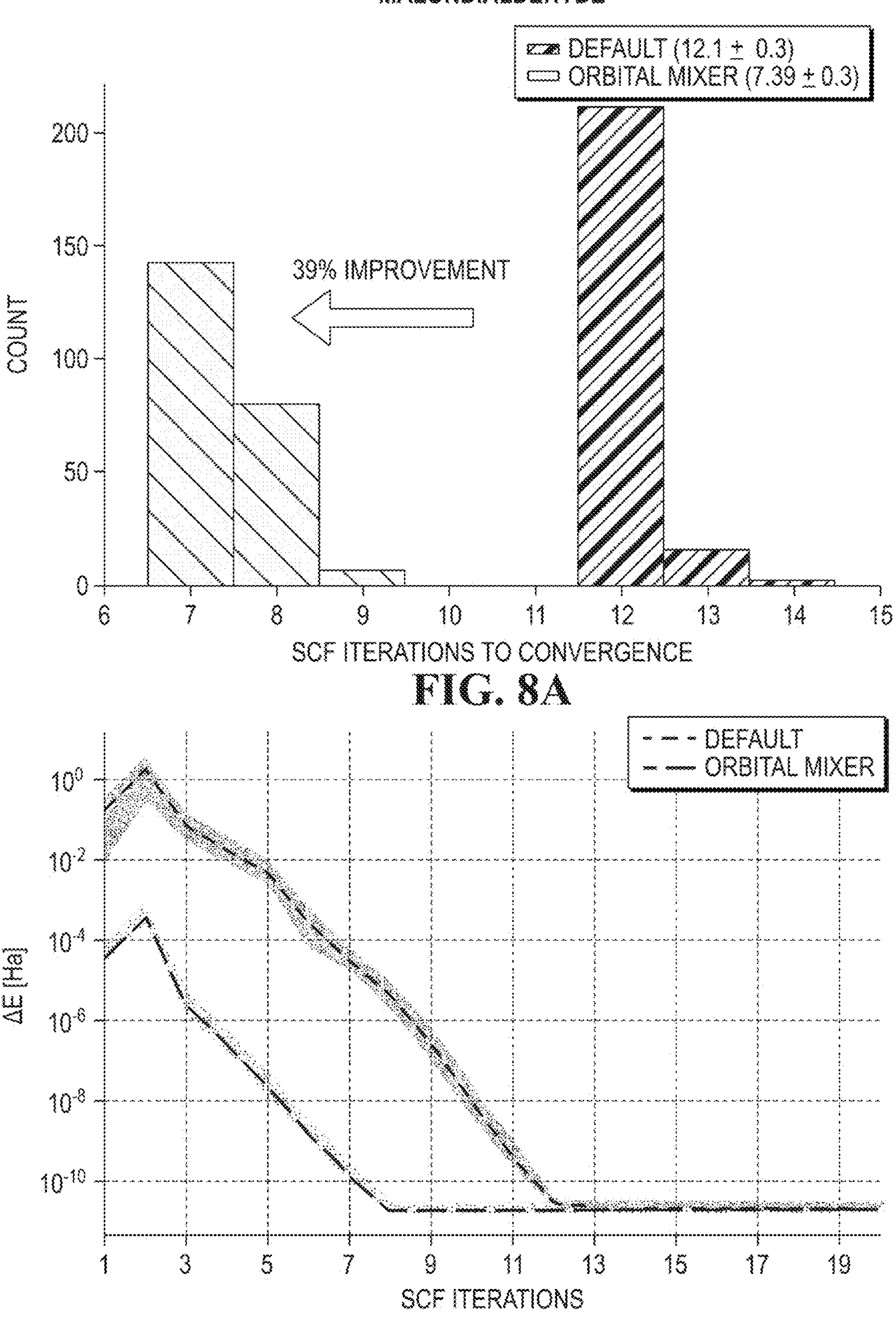
FIG. 8A is a graph that reports a distribution of SCF iterations to convergence for DFT calculations performed on 250 test set malondialdehyde configurations using both the default PySCF model and the orbital mixer model predicted Hamiltonian F for initialization.
FIG. 8B is a graph that tracks the difference in the total energy estimated after each SCF iteration as compared to the terminal converged energy estimate for malondialdehyde.

FIG. 8A is a graph that reports a distribution of SCF iterations to convergence for DFT calculations performed on 250 test set malondialdehyde configurations using both the default PySCF model and the orbital mixer model predicted Hamiltonian F for initialization. The orbital mixer model initialization achieves a 39% improvement in the number of SCF iterations required to reach convergence compared to the default PySCF model initialization strategy. FIG. 8B is a graph that tracks the difference in the total energy estimated after each SCF iteration as compared to the terminal converged energy estimate for malondialdehyde. Although both initialization schemes eventually reach the same energy difference criterion of $10^{-11}$ Ha, all configurations using the orbital mixer model initialization reliably converge after only at most 9 SCF iterations.

Figures 9A, 9B:
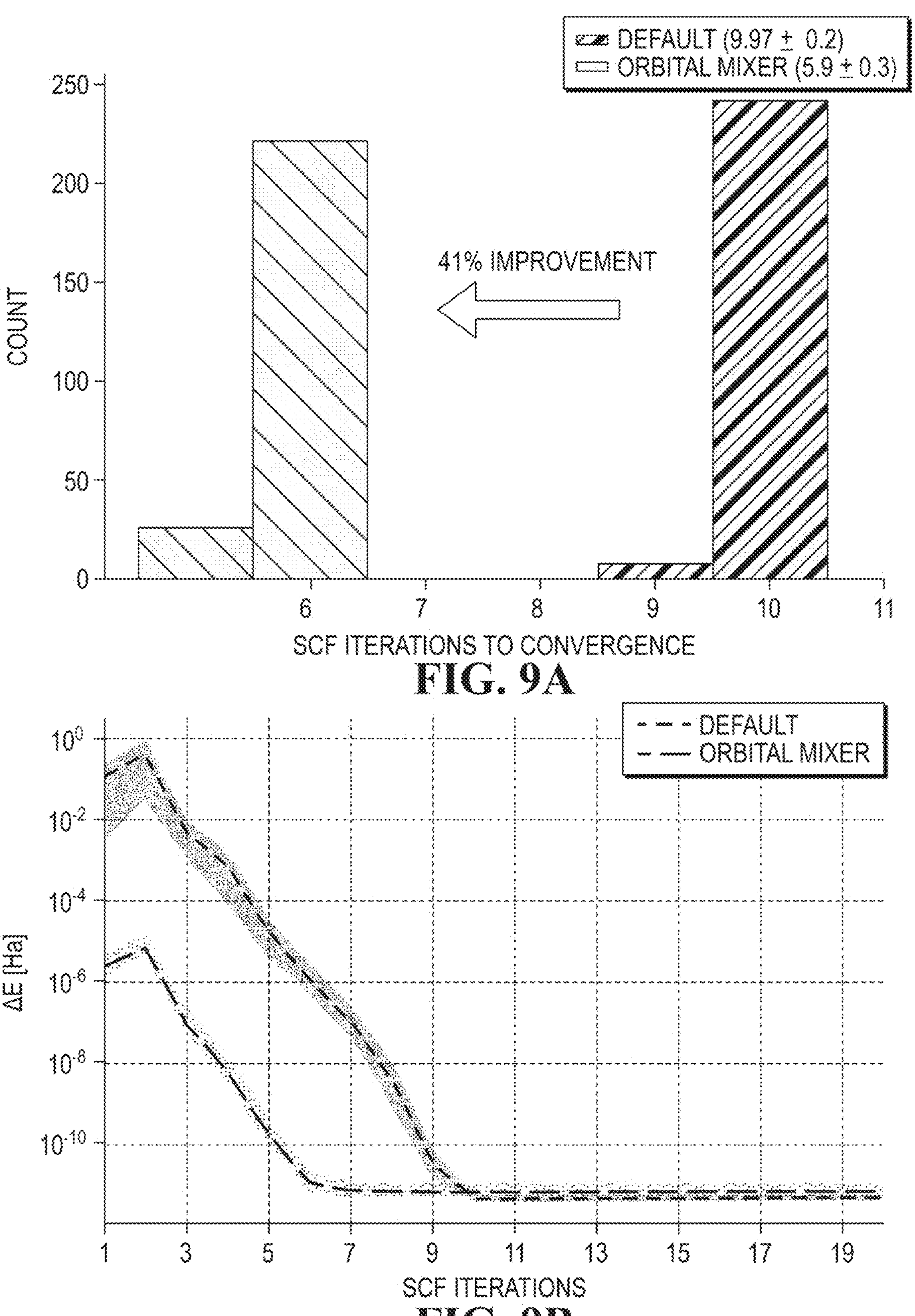
FIG. 9A is a graph that reports a distribution of SCF iterations to convergence for DFT calculations performed on 250 test set ethanol configurations using both the default PySCF model and the orbital mixer model predicted Hamiltonian F for initialization.
FIG. 9B is a graph that tracks the difference in the total energy estimated after each SCF iteration as compared to the terminal converged energy estimate for ethanol.
Figure 10A:
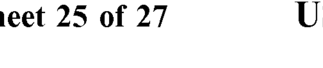
FIGS. 10A through 10H depict a comparison of highest occupied molecular orbital (HOMO) shapes for different molecular configurations (i.e., four random test configurations taken from uracil) derived from an orbital mixer model prediction and ground truth MO coefficients.
Figure 10A:
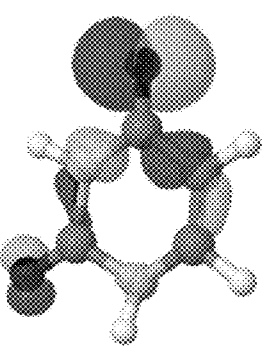
Figure 10B:
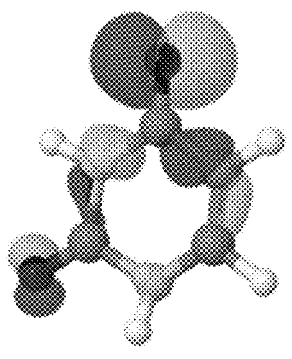
Figure 10C:
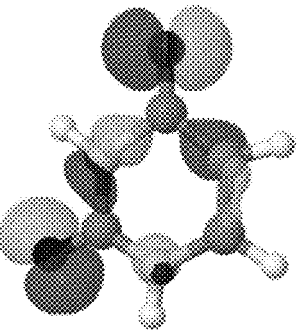
Figure 10D:
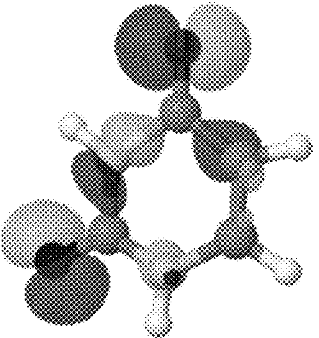
Figure 10E:
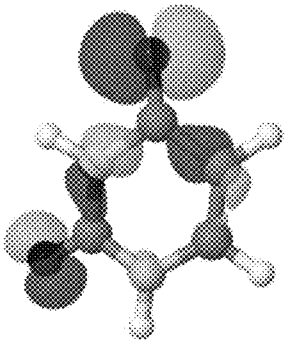
Figure 10F:
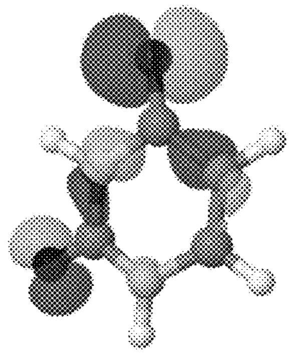
Figure 10G:
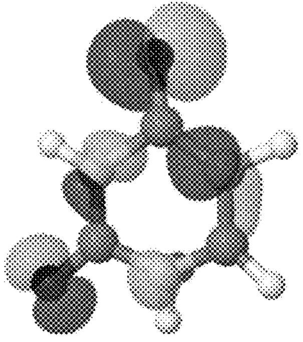
Figure 10H:
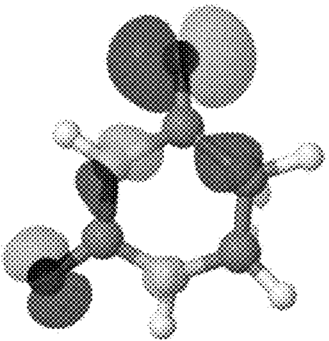
Figure 11A:
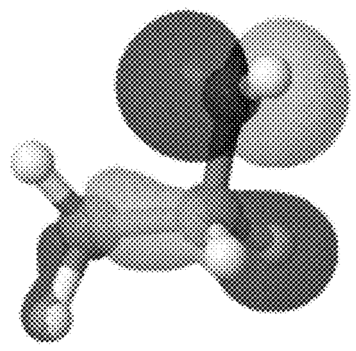
FIGS. 11A through 11H depict a comparison of HOMO shapes for different molecular configurations (i.e., four random test configurations taken from ethanol) derived from an orbital mixer model prediction and ground truth MO coefficients.
Figure 11B:
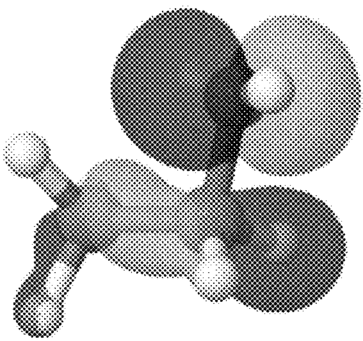
Figure 11C:
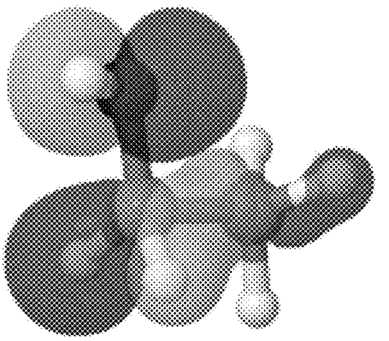
Figure 11D:
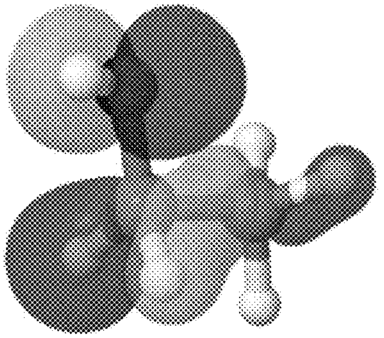
Figure 11E:
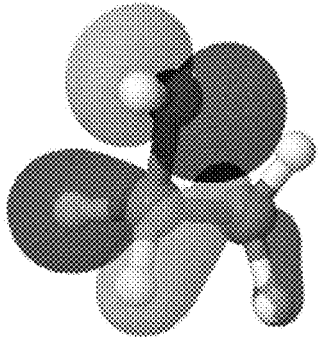
Figure 11F:
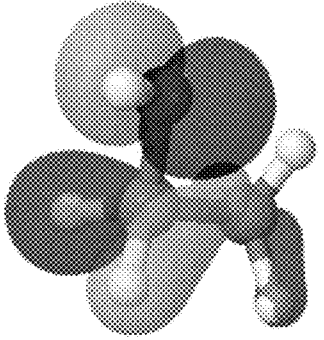
Figure 11G:
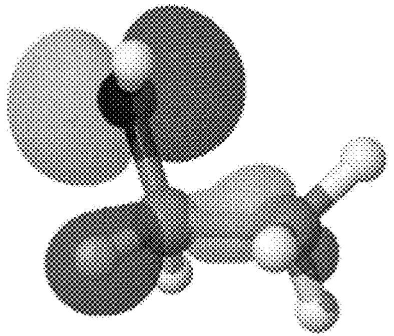
Figure 11H:
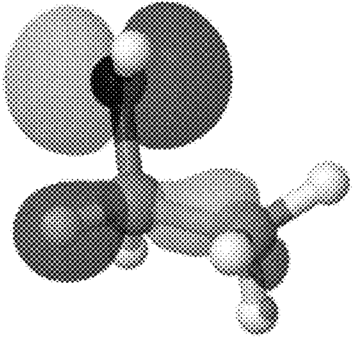
Figure 12A:
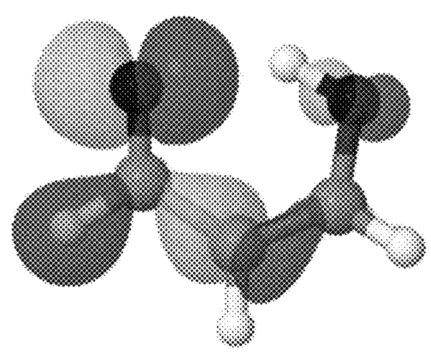
FIGS. 12A through 12H depict a comparison of HOMO shapes for different molecular configurations (i.e., four random test configurations taken from malondialdehyde) derived from an orbital mixer model prediction and ground truth MO coefficients.
Figure 12B:
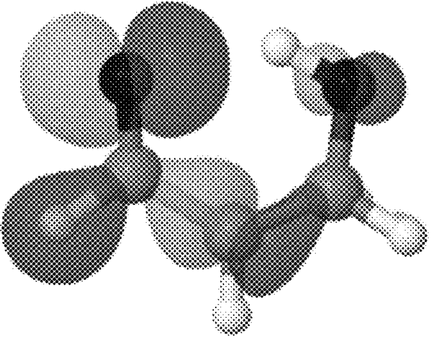
Figure 12C:
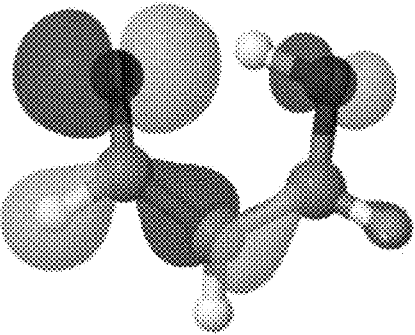
Figure 12D:
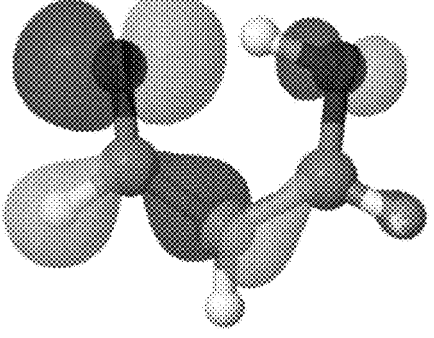
Figure 12E:
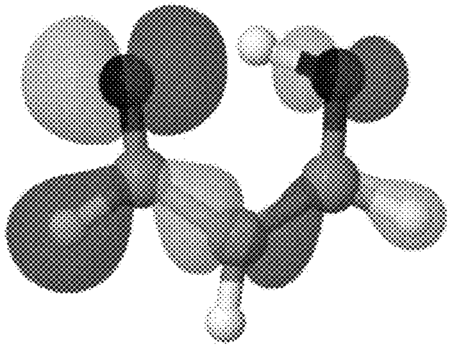
Figure 12F:
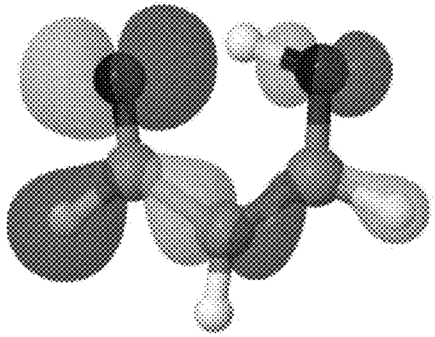
Figure 12G:
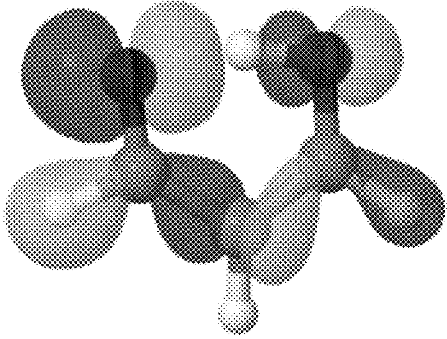
Figure 12H:
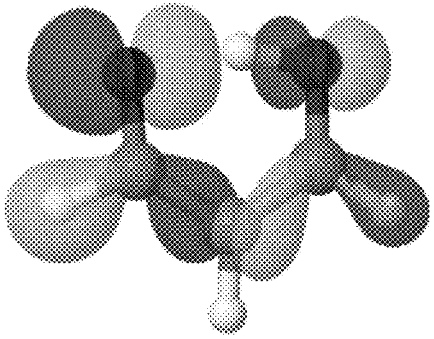

FIG. 9A is a graph that reports a distribution of SCF iterations to convergence for DFT calculations performed on 250 test set ethanol configurations using both the default PySCF model and the orbital mixer model predicted Hamiltonian F for initialization. The orbital mixer initialization achieves a 41% improvement in the number of SCF iterations required to reach convergence compared to the default PySCF model initialization strategy. FIG. 9B is a graph that tracks the difference in the total energy estimated after each SCF iteration as compared to the terminal converged energy estimate for ethanol. Although both initialization schemes eventually reach the same energy difference criterion of $10^{-11}$ Ha, all configurations using the orbital mixer model initialization reliably converge after only at most 7 SCF iterations.

Similar performance for other self-consistent field applications, from higher-accuracy quantum chemistry methods to inhomogeneous copolymers and nanoparticles is expected.

The capability of the orbital mixer model to directly calculate physical and chemical properties by using the orbital mixer predicted Hamiltonian F and molecular orbital coefficients to calculate HOMO-LUMO gaps and electronic dipole moments was investigated. HOMO-LUMO gaps and electronic dipole moments are physically meaningful and often measurable quantities. Table 2, reproduced below, reports a comparison of predicted HOMO-LUMO gap energies and dipole moments between the orbital mixer model and the SchNOrb model. The HOMO-LUMO gap energies and dipole moments are calculated with the PySCH model using the orbital mixer model predicted Hamiltonian F. The HOMO-LUMO gap was not reported in the original SchNOrb paper and are therefore calculated using retrained SchNOrb models. The dipole moments for the SchNOrb model are only reported at the 25K training set sizes reported in the original paper.

TABLE 2

| Molecule | Model (train size) | HOMO-LUMO gap [eV] | Dipole moment [D] |
|---|---|---|---|
| Ethanol | Orbital mixer (25K) | 0.0115 | 0.0071 |
| | SchNOrb (25K) | 0.0743 | 0.0262 |
| | Orbital mixer (950) | 0.0163 | 0.0103 |
| | SchNOrb (950) | 0.1190 | — |
| Malondialdehyde | Orbital mixer (25K) | 0.0061 | 0.0132 |
| | SchNOrb (25K) | 0.0384 | 0.0536 |
| | Orbital mixer (950) | 0.0083 | 0.0187 |
| | SchNOrb (950) | 0.1239 | — |
| Uracil | Orbital mixer (25K) | 0.0074 | 0.0227 |
| | SchNOrb (25K) | 0.4503 | 1.2762 |
| | Orbital mixer (950) | 0.0119 | 0.0336 |
| | SchNOrb (950) | 1.2780 | — |

The results for the orbital mixer model show overall excellent accuracies with respect to the reference DFT calculations for both HOMO-LUMO gap energies and dipole moments, at both training sizes MAEs below than 0.017 eV and 0.034 D, respectively. The orbital mixer model outperforms the SchNOrb model using fewer training data on the three benchmark molecules. The orbital mixer model performs particularly well on the most challenging molecule uracil. Using only 950 training samples, HOMO-LUMO gap energy and dipole moment predictions are generated with errors orders of magnitude smaller than those from a SchNOrb model trained with 25K configurations. These results highlight the ability of the orbital mixer model to capture chemically and physically meaningful molecular properties using a single neural network architecture, circumventing the development of separate specialized models for each property of interest.

One or more embodiments disclose a deep learning model for predicting molecular electronic structure directly in a basis of localized atomic orbitals. Compared to the SchNOrb model and the PhiSNet model, which generate predictions as a function of only atomic coordinates and molecular composition alone, the orbital mixer model of one or more embodiments leverages strong inductive biases by operating jointly on basis set-specific atomic orbital representations and the overlap matrix S to predict the Hamiltonian F for a molecular configuration. Unlike the PhiSNet model, which achieves explicit covariance using built-in SE(3)-equivalent operations, the orbital mixer model implicitly learns covariance similar to the SchNOrb model by training with data augmentation. The orbital mixer model benefits from a simple and intuitive architecture modelling interactions between atomic orbital representations using MLP mixers. Compared to the SchNOrb model, the orbital mixer model achieves upwards of 50% improvement in Hamiltonian F mean absolute errors and upwards of 95% improvement in predicting derived physical chemical properties while using about 10× fewer training samples. The built-in covariance of the PhiSNet model with respect to rigid molecular rotations and translations may additional be used for prediction ac curacy and therefore enables the PhiSNet model to achieve better reported Hamiltonian F MAE. In one or more embodiments, integrating the orbital mixer model into DFT workflows by purposing the orbital mixer predicted Hamiltonian F as an initial guess yields about 44% improvement in the number of SCF iterations required to reach convergence for uracil. The orbital mixer model scales well from the smallest molecule in the data set, ethanol, containing only 72 atomic orbitals, to the most challenging molecule, uracil, with 132 atomic orbitals. One or more embodiments represents an alternate approach for molecular electronic structure prediction leveraging a novel basis set dependent featurization within a simple MLP Mixer-enabled deep learning architecture.

In one or more embodiments, the orbital mixer model is evaluated on reference DFT calculations performed on ethanol, malondialdehyde and uracil molecule configurations extracted from the MD17 dataset available from Chmiela, S., Tkatchenko, A., Sauceda, H. E., Poltaysky, I., Schu¨tt, K. T., and Mu¨ller, K.-R. Machine learning of accurate energy-conserving molecular force fields. Science advances, 3(5): e1603015, 2017. Reference DFT calculations are performed on a subset of configurations that are used for training and evaluation in the SchNOrb paper (Schutt, K. T., Gastegger, M., Tkatchenko, A., Müller, K. R., and Maurer, R. J. Unifying machine learning and quantum chemistry with a deep neural network for molecular wavefunctions. Nature communications, 10(1):1-10, 2019). The DFT calculations are replicated as outlined in SchNOrb using the PySCF quantum chemistry code to generate our datasets. (Sun, Q., Berkelbach, T. C., Blunt, N. S., Booth, G. H., Guo, S., Li, Z., Liu, J., McClain, J. D., Sayfutyarova, E. R., Sharma, S., et al. Pyscf: the python-based simulations of chemistry framework. Wiley Interdisciplinary Reviews: Computational Molecular Science, 8(1):e1340, 2018). The def2-SVP basis set (Weigend, F. and Ahlrichs, R. Balanced basis sets of split valence, triple zeta valence and quadruple zeta valence quality for h to rn: Design and assessment of accuracy. Physical Chemistry Chemical Physics, 7(18):3297-3305, 2005) is used with the PBE exchange correlation functional (Perdew, J. P., Burke, K., and Ernzerhof, M. Generalized gradient approximation made simple. Physical review letters, 77(18):3865, 1996). All default PySCF procedures are used for performing SCF iterations based on the direct inversion in the iterative sub-space (DIIS) method (Pulay, P. Convergence acceleration of iterative sequences. the case of scf iteration. Chemical Physics Letters, 73(2): 393-398, 1980 and Pulay, P. Improved scf convergence acceleration. Journal of Computational Chemistry, 3(4):556-560, 1982) with default initial guesses generated using the 'MinAO' method (Sun et al., 2018) that considered a superposition of atomic densities projected onto the first contracted functions in the cc-pVTZ or cc-pVTZ-PP basis set. Each calculation uses a convergence criterion of $10^{-13}$ Ha total energy difference between consecutive iterations or a maximum of 50 SCF iterations.

The orbital mixer architecture of one or more embodiments uses a hidden dimension of $d_{hidden}$=1024 and GELU activation functions (Hendrycks, D. and Gimpel, K. Gaussian error linear units (gelus). arXiv preprint arXiv: 1606.08415, 2016). The initial row-wise MLP used to process the rows of the overlap matrix S includes two dense layers with an expansion factor of 2 for the intermediate hidden representation, such that the complete action of the MLP involves the following sequence of transformations onto the shape of the atomic orbital representations as set forth in equation (5):

$$N_{orbs} \rightarrow 2d_{hidden} \xrightarrow{GELU} d_{hidden} \quad (5)$$

The MPLs within the MLP Mixer layers for the overlap matrix and interaction branch similarly use an expansion factor of 2 with no dropout. The initial MLP Mixer applied to the overlap matrix S consists of $n_{layers}$=2 Mixer layers, while the second MLP Mixer applied to the atomic orbital embeddings used for predicting the Hamiltonian F within the interaction branch uses $n_{layers}$=6 mixer layer. The row-wise MLP used to reshape the $N_{orbs}$ $d_{hidden}$ representation processed by the MLP mixer in the interaction branch into the target $N_{orbs}\times N_{orbs}$ dimensionality consists of a GELU non-linearity followed by a single dense layer. The row-wise MLP in the diagonal correction branch similarly uses a GELU non-linearity followed by a single dense layer.

In one or more embodiments, the orbital mixer model is trained using an ADAM optimizer with the default PyTorch parameters and a mini-batch size of 32 samples. Evaluation and testing are performed using the model obtained with an exponential moving average over all parameters during training time employing a decay rate of 0.999 per step. Gradient clipping is applied to clip gradient norms to a maximum value of 0.001, as this helps to stabilize training. An initial learning rate of $3\times10^{-4}$ which is decayed by a factor of $\gamma$=0.8 every $n_{decay}$ training steps. The orbital mixer models may be trained for 120 hours on Nvidia Tesla V100 32 GB GPUs, after which time the training and validation losses are observed to plateau. When training reference SchNOrb models, the training procedures outlined in the SchNOrb paper are followed for the 25K dataset originally handled in the paper. The same training settings when training SchNOrb models on the 950 sample training set size are used, except the patience to decay the learning rate from the original 15 epochs when training with 25K samples is modified to 150 epochs when training with 950 samples. Training of SchNOrb models is still stopped in each case once the learning rate dropped below the $5\times10^{-6}$ threshold. Table 3 presented below includes a breakdown of these training settings and parameters for both the orbital mixer model and the retrained SchNOrb model.

TABLE 3

| Decay | Model (train size) | Val size | Test size | Batch Size | Initial learning rate | Scheduler (Decay LR by $\gamma$ = 0.8 . . .) |
|---|---|---|---|---|---|---|
| Ethanol | Orbital mixer (25K) | 50 | 4500 | 32 | $3\times10^{-4}$ | every $n_{decay}$ = 1M steps |
| | SchNOrb (25K) | 500 | 4500 | 32 | $3\times10^{-4}$ | after 15 epochs w/o val loss improvement |
| | Orbital mixer (950) | 50 | 4500 | 32 | $3\times10^{-4}$ | every $n_{decay}$ = 500K steps |
| | SchNOrb (950) | 50 | 4500 | 32 | $3\times10^{-4}$ | after 150 epochs w/o val loss improvement |
| Malondialdehyde | Orbital mixer (25K) | 50 | 1478 | 32 | $3\times10^{-4}$ | every $n_{decay}$ = 1M steps |
| | SchNOrb (25K) | 500 | 1478 | 32 | $3\times10^{-4}$ | after 15 epochs w/o val loss improvement |
| | Orbital mixer | 50 | 1478 | 32 | $3\times10^{-4}$ | every $n_{decay}$ = 300K |

TABLE 3-continued

| Decay | Model (train size) | Val size | Test size | Batch Size | Initial learning rate | Scheduler (Decay LR by $\gamma = 0.8$ . . .) |
|---|---|---|---|---|---|---|
| | (950) | | | | | steps |
| | SchNOrb (950) | 50 | 1478 | 32 | $3 \times 10^{-4}$ | after 150 epochs w/o val loss improvement |
| Uracil | Orbital mixer (25K) | 50 | 4500 | 32 | $3 \times 10^{-4}$ | every $n_{decay}$ = 1M steps |
| | SchNOrb (25K) | 500 | 4500 | 48 | $3 \times 10^{-4}$ | after 15 epochs w/o val loss improvement |
| | Orbital mixer (950) | 50 | 4500 | 32 | $3 \times 10^{-4}$ | every $n_{decay}$ = 500K steps |
| | SchNOrb (950) | 50 | 4500 | 48 | $3 \times 10^{-4}$ | after 150 epochs w/o val loss improvement |

FIGS. 10A through 10H depict a comparison of highest occupied molecular orbital (HOMO) shapes for different molecular configurations (i.e., four random test configurations taken from uracil) derived from an orbital mixer model prediction and ground truth MO coefficients. Each row is a different molecular configuration. FIGS. 10A, 10C, 10E, and 10G are the orbital mixer model prediction for each molecular configuration. FIGS. 10B, 10D, 10F, and 10H are the ground truth MO coefficients for each molecular configuration.

FIGS. 11A through 11H depict a comparison of HOMO shapes for different molecular configurations (i.e., four random test configurations taken from ethanol) derived from an orbital mixer model prediction and ground truth MO coefficients. Each row is a different molecular configuration. FIGS. 11A, 11C, 11E, and 11G are the orbital mixer model prediction for each molecular configuration. FIGS. 11B, 11D, 11F, and 11H are the ground truth MO coefficients for each molecular configuration.

FIGS. 12A through 12H depict a comparison of HOMO shapes for different molecular configurations (i.e., four random test configurations taken from malondialdehyde) derived from an orbital mixer model prediction and ground truth MO coefficients. Each row is a different molecular configuration. FIGS. 12A, 12C, 12E, and 12G are the orbital mixer model prediction for each molecular configuration. FIGS. 12B, 12D, 12F, and 12H are the ground truth MO coefficients for each molecular configuration.

Machine learning methods of one or more embodiments predict an electronic structure of an atomic system (e.g., a molecule). These machine learning methods may be useful for modeling chemical reaction mechanisms for materials used in fuel cells, water desalination devices, catalysis devices, coating systems, and/or batteries. The machine learning methods of one or more embodiments may be applied to practical effect to control one or more of these devices (e.g., fuel cells, water desalination devices, catalysis devices, coating systems, and/or batteries).

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as read-only memory (ROM) devices and information alterably stored on writeable storage media such as floppy disks, magnetic tapes, compact discs (CDs), RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A machine learning method for predicting an electronic structure of an atomic system, the method comprising:

receiving an atomic identifier and an atomic position for atoms in the atomic system;

receiving a basis set including rules for forming atomic orbitals of the atomic system;

forming the atomic orbitals of the atomic system; and predicting an electronic structure of the atomic system based on the atom identifier, the atom position for the atoms in the atomic system, and the atomic orbitals of the atomic system, the basis set and the atomic orbitals of the atomic system are introduced into the machine learning method during training such that the machine learning method predicts the electronic structure with a reduced number of self-consistent iterations with reduced computational expense.

2. The machine learning method of claim 1, further comprising forming an overlap matrix based on the atomic orbitals of the atomic system and the atomic positions for the atoms in the atomic system, where the overlap matrix includes entries $(i_n, j_n)$ between 0 and 1, the entries $(i_n, j_n)$ including entry (i,j) representing an overlap of atomic orbitals i and j $i_n$ space where 1 represents the i and j atomic orbitals are identical and 0 represents the i and j atomic orbitals do not overlap.

3. The machine learning method of claim 2, further comprising applying a linear transformation to rows of the overlap matrix to obtain an overlap matrix representation.

4. The machine learning method of claim 3, further comprising passing the overlap matrix representation through $L_1$ multi-layer perception (MLP) mixer layers.

5. The machine learning method of claim 4, further comprising determining a multi-feature embedding for one or more of the atomic orbitals by embedding categorical features of each of the atomic orbitals to form a set of embedded categorical features and summing the set of embedded categorical features to obtain multi-feature atomic orbital embeddings.

6. The machine learning method of claim 5, further comprising summing the multi-feature atomic orbital embeddings and the overlap matrix representation to obtain a molecular representation.

7. The machine learning method of claim 6, further comprising applying a linear transformation to rows of the molecular representation to obtain a diagonal correction term.

8. The machine learning method of claim 7, further comprising passing the molecular representation through $L_2$ MLP mixer layers to obtain a mixer layer output, the $L_2$ MLP mixer layers are in addition to the $L_1$ MLP mixer layers, and applying a linear transformation to the mixer layer output to obtain a refined molecular representation.

9. The machine learning method of claim 8, further comprising adding the diagonal correction term and the diagonal of the refined molecular representation to obtain a diagonal-corrected refined molecular representation.

10. The machine learning method of claim 9, further comprising adding a transpose of the diagonal-corrected refined molecular representation to the diagonal-corrected refined molecular representation to obtain a predicted Hamiltonian matrix indicative of the electronic structure of the atomic system.

11. The machine learning method of claim 1, wherein the machine learning method is a deep neural network learning method.

12. A machine learning training method for training parameters of a machine learning model for predicting an electronic structure of an atomic system, the method comprising:
- receiving a true electronic structure of the atomic system;
- receiving a basis set including rules for forming first and second atomic orbitals of the atomic system;
- predicting a predicted electronic structure of the atomic system by performing a forward pass through the machine learning model using the basis set;
- determining a loss by comparing the true electronic structure and the predicted electronic structure of the atomic system; and
- training the machine learning model by updating the parameters of the machine learning model based on the loss and a machine learning optimizer, the basis set and the atomic orbitals of the atomic system are introduced into the machine learning model during training such that the machine learning model predicts the electronic structure with a reduced number of self-consistent iterations with reduced computational expense.

13. The machine learning training method of claim 12, further comprising controlling a device utilizing the first and second atomic systems depending on the updated parameters of the machine learning model.

14. The machine learning training method of claim 12, wherein the machine learning model is a deep neural network.

15. The machine learning training method of claim 14, wherein the deep neural network is modified by a deep neural network modification.

16. The machine learning training method of claim 15, wherein the deep neural network modification is selected from the group consisting of: dropout, batch normalization, layer normalization, and weight decay.

17. The machine learning training method of claim 12, wherein the machine learning model has a multi-layer perception (MLP) mixer layer.

18. A machine learning method for predicting molecular orbital characteristics of a molecule, the method comprising:
- receiving atomic positions and atomic identifiers of atoms in the molecule;
- receiving a basis set including rules for forming atomic orbitals of the molecule;
- predicting a predicted electronic structure and calculating an overlap matrix of the molecule by performing a forward pass using the atomic positions, the atomic identifiers, and the basis set; and
- predicting the molecular orbital characteristics based on the predicted electronic structure and the overlap matrix, the basis set and the atomic orbitals of the atomic system are introduced into the machine learning method during training such that the machine learning method predicts the electronic structure with a reduced number of self-consistent iterations with reduced computational expense.

19. The machine learning method of claim 18, wherein the molecular orbital characteristics include molecular orbital coefficients and/or molecular orbital energies.

20. The machine learning method of claim 18, wherein the second predicting step uses the predicted electronic structure and the overlap matrix to solve the eigenvalue problem of $\hat{F}C=SCE$ to obtain the molecular orbital characteristics.

* * * * *